United States Patent [19]
Wierzbicki et al.

[11] Patent Number: 5,629,339
[45] Date of Patent: May 13, 1997

[54] DIOSMETIN COMPOUNDS

[75] Inventors: Michel Wierzbicki, L'Etang la Ville; Marie-Françoise Boussard, Mareil sur Mauldre; Tony Verbeuren, Vernouillet; Marie-Odile Vallez, Champs sur Marne; Emmanuel Canet, Paris; Yves Rolland, Vanves, all of France

[73] Assignee: Adir et Compagnie, Courbevoie, France

[21] Appl. No.: 547,650

[22] Filed: Oct. 24, 1995

[30] Foreign Application Priority Data

Oct. 26, 1994 [FR] France ................... 94 12783

[51] Int. Cl.⁶ .................. A61K 31/35; C07D 311/30
[52] U.S. Cl. ........................... 514/456; 549/403
[58] Field of Search ................ 549/403; 514/456

[56] References Cited

FOREIGN PATENT DOCUMENTS 0644374 7/1984 Switzerland.
0928150 6/1963 United Kingdom.

OTHER PUBLICATIONS

Elliger et al. (CA 100:187028) 1984.
Geiger et al. (CA 101:6889) 1984.
Wolfbeis et al. (CA 109:110080) 1988.
Yasukawa et al. (CA 111:49912) 1989.
Boutin et al. (CA 120:94635) 1994.
Boutin et al. (CA 122;10460) 1995.

*Primary Examiner*—Johann Richter
*Assistant Examiner*—Laura L. Stockton
*Attorney, Agent, or Firm*—The Firm of Gordon W. Hueschen

[57] ABSTRACT

Disclosed herein are new diosmetin compounds of formula:

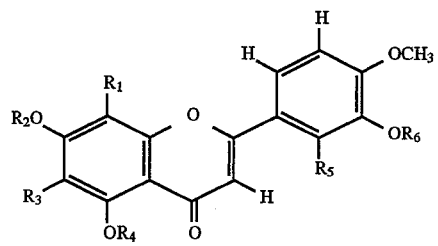

wherein $R_1$, $R_2$, $R_3$, $R_4$, $R_5$ and $R_6$ are as defined in the description.

The said compounds are useful in the treatment of chronic venous insufficiency.

22 Claims, No Drawings

DIOSMETIN COMPOUNDS

The present invention relates to new diosmetin compounds, a process for their preparation and pharmaceutical compositions containing them.

It relates more especially to compounds of formula I:

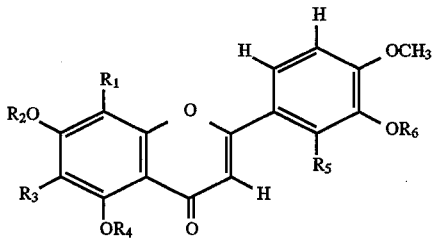

wherein:

$R_1$ represents a hydrogen atom or a propyl, allyl or 1,2-dideuteroallyl radical;

$R_2$ represents a hydrogen atom or a propyl, allyl, propargyl, 2,3-dihydroxypropyl, (2,2-dimethyl-1,3-dioxol-4-yl)methyl or 3-acetoxy-2-hydroxypropyl radical;

$R_3$ represents a hydrogen atom or a propyl, allyl or 1,2-dideuteroallyl radical;

$R_4$ represents a hydrogen atom, a methyl, propyl, allyl, propargyl, 2,3-dihydroxypropyl or (2,2-dimethyl-1,3-dioxol-4-yl)methyl radical or a radical of the formula -COR'$_4$ [wherein R'$_4$ represents an alkyl radical having from 1 to 5 carbon atoms inclusive in straight or branched chain or a phenyl radical];

$R_5$ represents a hydrogen atom or a propyl, allyl or 1,2-dideuteroallyl radical, and $R_6$ represents a hydrogen atom, a methyl, propyl, allyl, propargyl, 2,3-dihydroxypropyl or (2,2-dimethyl-1,3-dioxol-4-yl)methyl radical, a radical of the formula -COR'$_6$ [wherein R'$_6$ represents an alkyl radical having from 1 to 5 carbon atoms inclusive in straight or branched chain or a phenyl radical] or a radical of the formula:

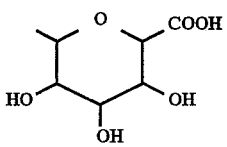

with the proviso that:

at least one of the radicals $R_1$, $R_2$, $R_3$, $R_4$, $R_5$ and $R_6$ has a meaning other than hydrogen, and that if $R_1$, $R_2$ and $R_3$ each simultaneously represent a hydrogen atom, then $R_4$ also represents a hydrogen atom;

and also their diastereoisomers and/or enantiomers, when they exist.

Certain compounds of formula I exist in several crystalline forms, some of which are especially valuable where the active ingredient is administered in solid form (tablet, suspension or suppository). Those different forms, as such, form part of the present invention.

The prior art is illustrated especially by the patent specification EP 0 319 412, which relates to substituted 2-piperazinyl-2-oxoethylene flavonoid compounds, which can be used in the treatment of vascular disorders.

The ever-increasing occurrence of those disorders justifies a favourable welcome to any invention of medicaments in that field. It is within that framework that the present invention is presented, relating to a family of products of chemical structures well differentiated from those of prior known active ingredients, and having pharmacological and therapeutic properties especially valuable in the treatment of the said disorders.

The presence of a specific venous capillary microangiopathy has been demonstrated in chronic venous insufficiencies. That microangiopathy, which is the result of venous hypertension, leads to venous capillary filtration disorders (hyperpermeability) and thus micro-oedemas (Barbier et al., La Presse Médicale, 23: p 213–224, 1994). The improvement of microcirculatory disorders that accompany chronic venous insufficiency (oedema, inflammation) ought to form part of the medicament treatment of that disorder (Chauveau, La Presse Médicale, 23: p243–249, 1994).

It has now been found, within the departments of the Applicant, that the compounds of the present invention not only have an anti-inflammatory activity—demonstrated in conventional inflammation models—but also, and above all, an anti-hyperpermeability activity, demonstrated using modem microscopy techniques to evaluate the responses of the microcirculation, cf Bjork et at., Progr. Appl. Microcircul., 6, 41–53, (1984). Thus, the compound of the present invention can be used especially in the treatment of chronic venous insufficiency.

The present invention relates also to pharmaceutical compositions comprising as active ingredient a compound of formula I or a physiologically tolerable salt thereof, mixed with or in association with one or more appropriate pharmaceutical excipients.

The pharmaceutical compositions so obtained are generally presented in dosage form containing from 1 to 500 mg of active ingredient. They may, for example, be in the form of tablets, dragées, gelatin capsules, suppositories or injectable or drinkable solutions and may be administered by the oral, rectal or parenteral route.

The dosage may vary, especially in accordance with the age and weight of the patient, the administration route, the nature of the disorder and associated treatments, and ranges from 1 to 500 mg of active ingredient from 1 to 6 times per day.

The compounds of formula I are all prepared from diosmetin, using conventional chemical methods employing, for example, depending on the case in question, alkylation, transposition, esterification, hydrogenation, hydrogenolysis and/or hydrolysis reactions, as illustrated in schemes 1 to 19.

The present invention relates also to a process for the preparation of compounds of formula I which is characterised in that diosmetin of formula II:

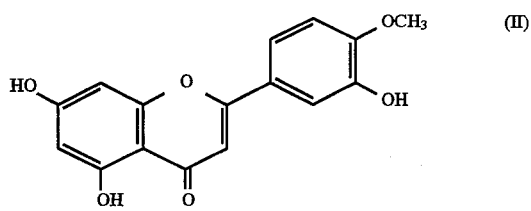

is treated:

A/either with a compound of formula III:

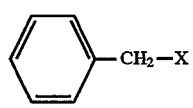

wherein X represents a halogen atom, such as, for example, a chlorine or bromine atom, or a tosyloxy radical, to obtain a compound of formula IV:

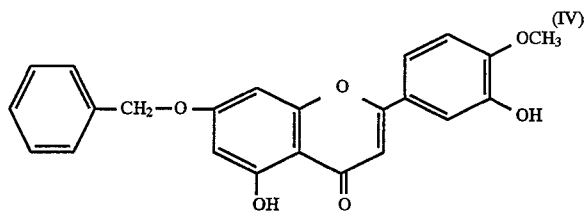

which is treated:
a) either with an allyl halide of formula H₂C=CH—CH₂-Hal wherein Hal represents a chlorine or bromine atom, to yield a compound of formula V:

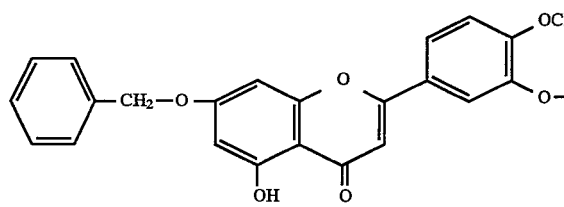

which, by transposition, yields the compound of formula VI:

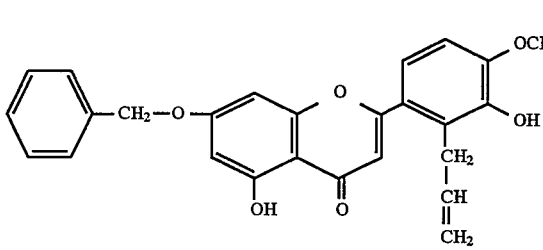

which, by hydrogenation, yields the compound of formula Ia:

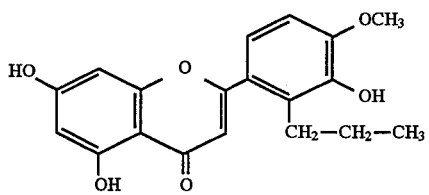

which, treated in turn with an allyl halide of formula H₂C=CH—CH₂-Hal wherein Hal represents a chlorine or bromine atom, yields the compound of formula (Ib):

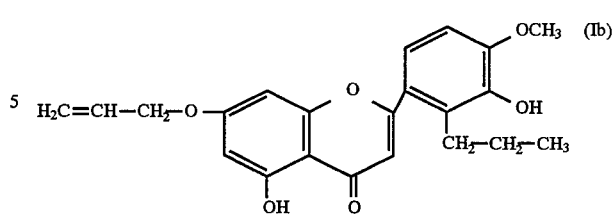

which, by hydrogenation, yields the compound of formula Ic:

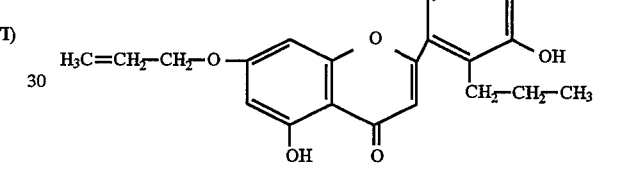

b) or with (2,2-dimethyl-1,3-dioxol-4-yl)methyl tosylate of formula:

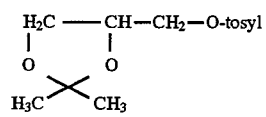

to yield the compound of formula VII:

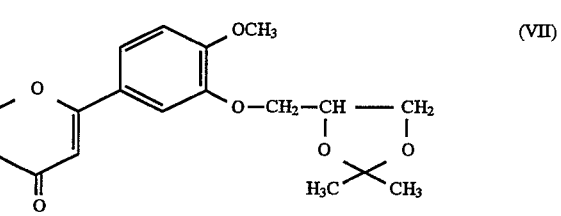

which, by hydrogenation, yields the compound of formula Id:

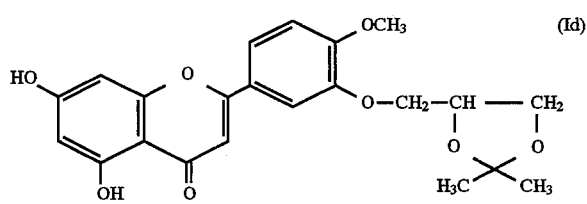

which, treated with acetic acid and H$_2$O yields the compound of formula Ie:

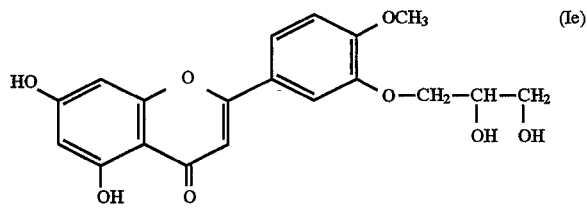

B/with a compound of formula III':

R'$_2$—X  (III')

wherein:
R'$_2$ represents an allyl or (2,2-dimethyl-1,3-dioxol-4-yl)methyl or propargyl radical, and
X is as defined above, to obtain, depending on the quantity of compound III' in relation to that of compound II, one or other of the compounds of formulae If, Ig and Ih:

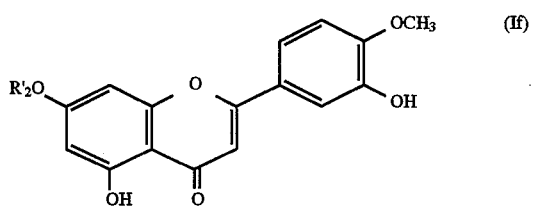

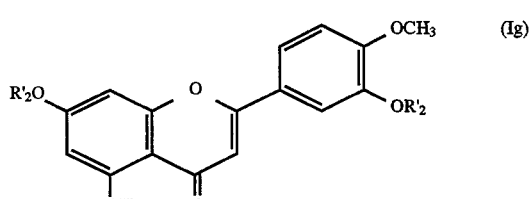

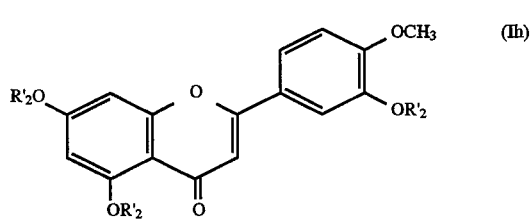

which compounds may be subjected to subsequent reactions selected from alkylation, transposition, esterification, reduction with hydrogen or deuterium and hydrolysis (as illustrated in the attached schemes) to yield products of formula I other than those of formulae Ia to Ih the preparation of which is described above.

The totality of the compounds so prepared forms the totality of the compounds of formula I. The following Examples illustrate the present invention.

EXAMPLE 1

7-Allyloxy-5-hydroxy-2-(3-hydroxy-4-methoxyphenyl)-4H-1-benzopyran-4-one

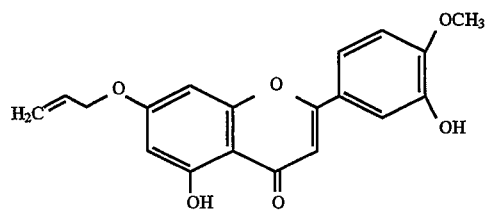

10 g of potassium hydrogen carbonate and then, dropwise, 11 g of allyl bromide, are added with stirring to 30 g of diosmetin which have been placed in 200 ml of anhydrous dimethylformamide and heated to 80° C. Stirring is maintained at 80° C. for 8 hours, and then the whole is allowed to return to room temperature and the reaction mixture is filtered.

The residue obtained is recrystallised from isopropanol, yielding 18.5 g of the expected compound of approximately 95% purity.

An analytical sample was obtained by chromatography on silica using a dichloromethane/methanol mixture (98/2) as eluant; m.p.: 174° C.

EXAMPLE 2

7-Allyloxy-5-hydroxy-2-(3-allyloxy-4-methoxyphenyl)-4H-1-benzopyran-4-one

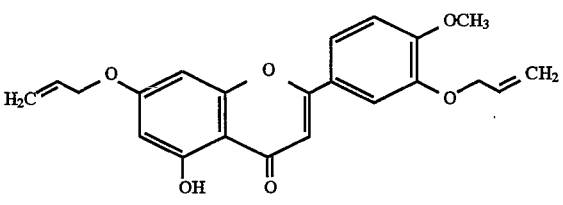

20 g of potassium hydrogen carbonate and then, dropwise, 21 g of allyl bromide, are added to 30 g of diosmetin placed in 200 ml of dimethylformamide and heated to 80° C. Heating and stirring are maintained for 12 hours after the addition is complete, and then the whole is allowed to return to room temperature and the reaction mixture is filtered. After that, the solvent is distilled off under reduced pressure and the residue is recrystallised from isopropanol, yielding 30 g of the expected compound, m.p.: 122° C.

EXAMPLE 3

5,7-Diallyloxy-2-(3-allyloxy-4-methoxyphenyl)-4H-1-benzopyran-4-one

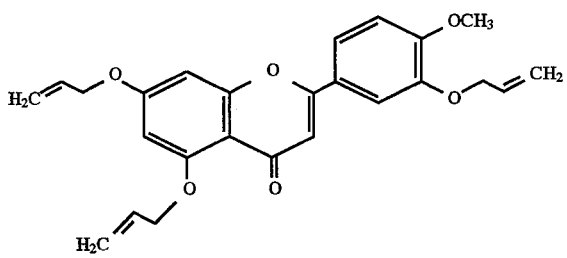

30 g of diosmetin in 300 ml of dimethylformamide are added to a suspension of 11.7 g of sodium hydride in 150 ml of dimethylformamide. The mixture is maintained at 40° C. with stirring until the evolution of gas has ceased. 48 g of allyl bromide are then added and stirring at 40° C. is continued for 22 hours.

The solvents and volatile products are distilled off under reduced pressure. The residue is taken up in chloroform for 2 hours at 20° C. The sodium bromide is then filtered off. The chloroform solution is concentrated to dryness and the residue is recrystallised from isopropanol. 29.4 g of the expected compound are obtained, m.p.: 125° C.

EXAMPLE 4

(R,S)-5-Hydroxy-7-[(2,2-dimethyl-1,3-dioxol-4-yl)methoxy]-2-(3-hydroxy-4-methoxyphenyl)-4H-1-benzopyran-4-one

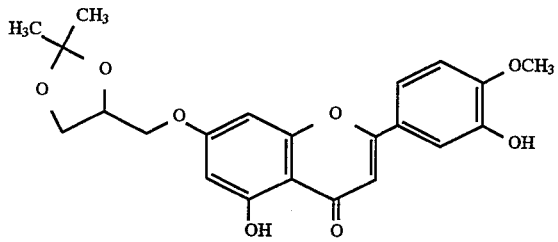

31.5 g of (R,S)-(2,2-dimethyl-1,3-dioxol-4 yl)methyl p-toluenesulphonate are added dropwise, with stirring, to 30 g of diosmetin and 11.5 g of potassium hydrogen carbonate in 200 ml of dimethylformamide heated to 90° C. Heating and stirring are then maintained for 24 hours and the reaction mixture is subsequently filtered. The filtrate is concentrated to dryness by distilling off the dimethylformamide under reduced pressure, and the residue is taken up in dichloromethane. The solution so obtained is concentrated to dryness and the residue is recrystallised twice from isopropanol, yielding 22 g of the expected compound, m.p.: 180° C.

EXAMPLES 5 AND 6

The compounds forming the subject of the following Examples were prepared by proceeding as described in Example 4:

5) (R)-5-Hydroxy-7-[(2,2-dimethyl-1,3-dioxol-4-yl)methoxy]-2-(3-hydroxy-4-methoxyphenyl)-4H-1-benzopyran-4-one, m.p.: 142° C., starting from (2,2-dimethyl-1,3-dioxol-4-yl)methyl p-toluenesulphonate in the form of the S isomer.

6) (S)-5-Hydroxy-7-[(2,2-dimethyl-1,3-dioxol-4-yl)methoxy]-2-(3-hydroxy-4-methoxyphenyl)-4H-1-benzopyran-4-one, m.p.: 142° C., starting from (2,2-dimethyl-1,3-dioxol-4-yl)methyl p-toluenesulphonate in the form of the R isomer.

EXAMPLE 7

5-Hydroxy-7-[(2,2-dimethyl-1,3-dioxol-4-yl)methoxy]-2-{3-[(2,2-dimethyl-1,3-dioxol-4-yl)methoxy]-4-methoxyphenyl}-4H-1-benzopyran-4-one

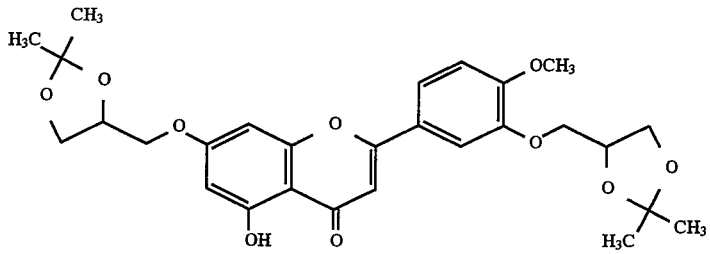

30 g of diosmetin, 22 g of potassium hydrogen carbonate and 56 g of (2,2-dimethyl-1,3-dioxol-4-yl)methyl p-toluenesulphonate in 500 ml of dimethylformamide to which 25 ml of hexamethylphosphoramide have been added are heated at 80° C., with stirring, for 30 hours. The solvents and volatile products are then distilled off under reduced pressure and the residue is subsequently taken up in 500 ml of dichloromethane. The salt which crystallises is removed by filtration, the organic phase is concentrated to dryness by distillation and the residue is recrystallised from anhydrous isopropanol, yielding 25.2 g of product of 95% purity which can be used as it is.

A pure sample of the expected product was prepared by chromatography on silica, using as eluant a $CH_2Cl_2/CH_3OH$ mixture progressively concentrated to 5% $CH_3OH$, m.p.: 155°–156° C.

EXAMPLE 8

5,7-Di-[(2,2-dimethyl-1,3-dioxol-4-yl)methoxy]-2-{3-[(2,2-dimethyl-1,3-dioxol-4-yl)methoxy]-4-methoxyphenyl}-4H-1-benzopyran-4-one

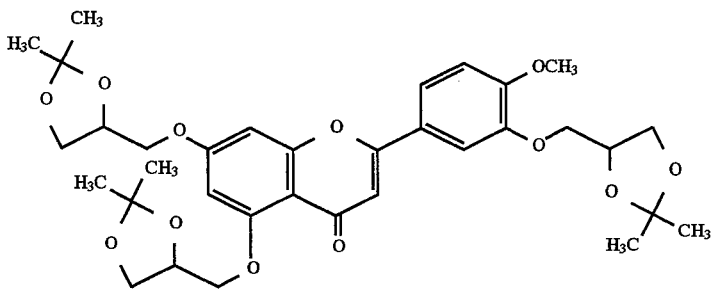

30 g of diosmetin and 10 g of sodium hydride are stirred at room temperature in 100 ml of anhydrous dimethylformamide. When the evolution of gas has ceased, 100 g of (2,2-dimethyl-1,3-dioxol-4-yl)methyl p-toluenesulphonate dissolved in 200 ml of dimethylformamide are slowly added to the reaction mixture. The whole is then heated at 80° C., with stirring, for 72 hours, after which the solvent is removed by distillation under reduced pressure and the residue is taken up in a mixture of dichloromethane, methanol and diethyl ether. After filtration of the insoluble components, the filtrate is concentrated to dryness and the residue is recrystallised from isopropanol, yielding 22 g of a fluorescent compound of 94% purity which can be used as it is. An analytical sample of the expected product was obtained by chromatography on silica, using as eluant a $CH_2Cl_2/CH_3OH$ mixture progressively concentrated to 5% $CH_3OH$.

EXAMPLE 9

5,7-Dihydroxy-2-{3-[(2,2-dimethyl-1,3-dioxol-4-yl)methoxy]-4-methoxyphenyl}-4H-1-benzopyran-4-one

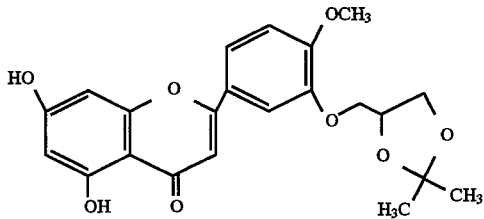

A) Step A

7-Benzyloxy-5-hydroxy-2-{3-[(2,2-dimethyl-1,3-dioxol-4-yl)methoxy]-4-methoxyphenyl}-4H-1-benzopyran-4-one.

39 g of 7-O-benzyldiosmetin and 10 g of potassium hydrogen carbonate in 300 ml of dimethylformamide are heated to 90° C., with stirring, and those conditions are maintained for 2 hours, after which the temperature is adjusted to 80° C. and there is added dropwise to that mixture a solution of 31 g of (2,2-dimethyl-1,3-dioxol-4-yl) methyl p-toluenesulphonate in 150 ml of dimethylformamide. The mixture is maintained at 80° C., with stirring, for 24 hours, and then the solvent is distilled off under reduced pressure and the residue is taken up in dichloromethane. The insoluble components are then filtered off, the filtrate is concentrated to dryness and the residue is recrystallised from isopropanol, yielding 45 g of the expected compound of 95% purity which can be used as it is.

B) Step B 5,7-Dihydroxy-2-{3-[(2,2-dimethyl-1,3-dioxol-4-yl)methoxy]-4-methoxyphenyl}-4H-1-benzopyran-4-one.

The 45 g of compound obtained in Step A are placed in 300 ml of dimethylformamide and subjected to catalytic hydrogenolysis, under a pressure of 6300 hPa, in the presence of 300 mg of 5% palladium-on-carbon.

When the theoretical amount of hydrogen has been absorbed, the reaction mixture is filtered, the solvents are removed by distillation and the residue obtained, that is, 36 g of the expected compound, is used as it is.

EXAMPLE 10

5,7-Dihydroxy-2-[3-(2,3-dihydroxypropoxy)-4-methoxyphenyl]-4H-1-benzopyran-4-one

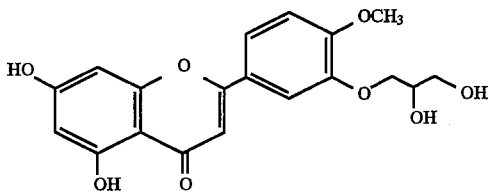

The 36 g of compound obtained in Example 9 are added to 200 ml of a mixture of water and acetic acid (1/1) and the whole is heated at reflux until the mixture becomes homogeneous, after which refluxing is maintained for a further 15 minutes. The disappearance of the acetonide is verified by thin-layer chromatography, then the mixture is cooled to 0° C., and the precipitate formed is filtered and then dried, yielding 30 g of the expected compound of 98% purity. Recrystallisation of that compound from a mixture of isopropanol and water yields the pure product, m.p.: 215°–218° C.

EXAMPLE 11

5,7-Dihydroxy-2-(3-hydroxy-4-methoxy-2-propylphenyl)-4H-1-benzopyran-4-one

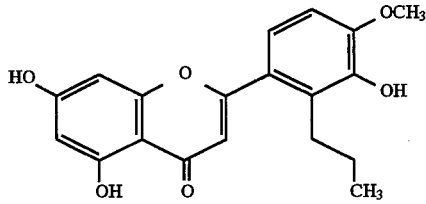

A) Step A

7-Benzyloxy-5-hydroxy-2-(3-allyloxy-4-methoxyphenyl)-4H-1-benzopyran-4-one.

39 g of 7-O-benzyldiosmetin and 11 g of potassium hydrogen carbonate in 300 ml of dimethylformamide are heated to and then maintained at 90° C. for two hours with stirring. The reaction mixture is then allowed to return to room temperature and 16 g of allyl bromide dissolved in 100 ml of dimethylformamide are subsequently slowly added.

The whole is heated to 60° C. and maintained at that temperature for 36 hours. The volatile components are then distilled off under reduced pressure and the residue is taken up in dichloromethane. The insoluble salts are then filtered and the filtrate is concentrated to dryness, yielding 40 g of the expected compound which can be used as it is. An analytical sample was prepared by recrystallisation from isopropanol, m.p.: 219° C.

B) Step B

7-Benzyloxy-5-hydroxy-2-(2-allyl-3-hydroxy-4-methoxyphenyl)-4H-1-benzopyran-4-one.

The 40 g of compound from Step A are added to 300 ml of trichlorobenzene. The whole is heated at reflux for 1 hour 30 minutes, then cooled to room temperature, and petroleum ether is added until precipitation is complete. The oil obtained solidifies after a few hours' stirring. The crystals are collected by filtration and washed with petroleum ether yielding 38 g of the expected compound, which is used as it is. An analytical sample was prepared by recrystallisation from isopropanol, m.p.: 234° C.

C) Step C 5,7-Dihydroxy-2-(3-hydroxy-4-methoxy-2-propylphenyl)-4H-1-benzopyran-4-one.

The 38 g of final compound obtained in Step B placed in 350 ml of dimethylformamide are subjected to a hydrogen pressure of 6300 hPa in the presence of 300 mg of 5% palladium-on-carbon as catalyst. When the theoretical amount of hydrogen has been absorbed, the reaction mixture is filtered, the filtrate is distilled under reduced pressure and the residue is recrystallised from isopropanol, yielding 25 g of the expected product, m.p.: 200° C.

EXAMPLE 12

5-Hydroxy-7-[(2,2-dimethyl-1,3-dioxol-4-yl)methoxy]-2-(3,4-dimethoxyphenyl)-4H-1-benzopyran-4-one

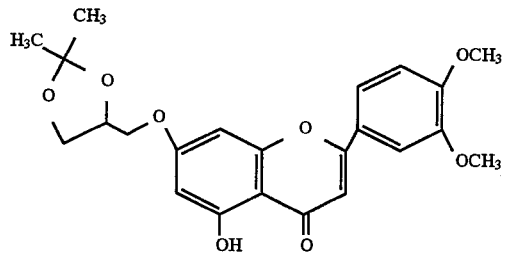

41 g of (R,S)-5-hydroxy-7-[(2,2-dimethyl-1,3-dioxol-4-yl)methoxy]-2-(3-hydroxy-4-methoxyphenyl)-4H-1-benzopyran-4-one, prepared in accordance with Example 4, are stirred in 800 ml of dimethylformamide with 20 g of potassium hydrogen carbonate at a temperature of 100° C. until the evolution of gas has ceased. The mixture is then cooled to 40° C. and 20.5 g of methyl iodide are subsequently added dropwise. When the addition is complete, stirring is continued for one hour. The solvent and the volatile products are then distilled off under reduced pressure. The residue is taken up in a minimum amount of dichloromethane and the solution is filtered over 400 g of silica using as eluant a $CH_2Cl_2/CH_3OH$ mixture progressively concentrated to 5% $CH_3OH$. Evaporation of the solvent yields 30 g of the expected compound, which can be used as it is. An analytical sample was prepared by recrystallisation from isopropanol, m.p.: 166° C.

EXAMPLE 13

5-Hydroxy-2-(3,4-dimethoxyphenyl)-7-(2,3-dihydroxypropoxy)-4H-1-benzopyran-4-one

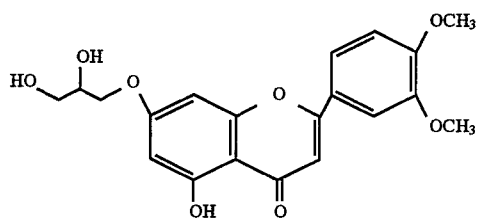

The 30 g of compound prepared in Example 12 are hydrolysed as described in Example 10. After a first recrystallisation from isopropanol and then a second recrystallisation from acetonitrile, 22 g of the expected product are obtained in pure form, m.p.: 149° C.

EXAMPLE 14

5-Methoxy-7-[(2,2-dimethyl-1,3-dioxol-4-yl)methoxy]-2-(3,4-dimethoxyphenyl)-4H-1-benzopyran-4-one

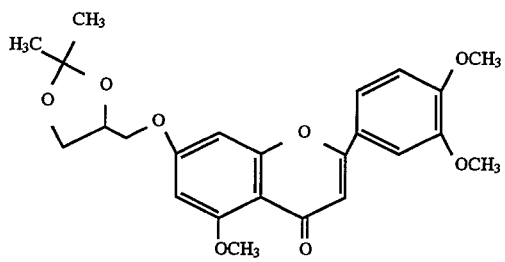

41 g of (R,S)-5-hydroxy-7-[(2,2-dimethyldioxol-4-yl)methoxy]-2-(3-hydroxy-4-methoxyphenyl)-4H-1-benzopyran-4-one, prepared in accordance with Example 4, are stirred in 800 ml of dimethylformamide with 40 g of potassium carbonate, at a temperature of 100° C., until the evolution of gas has ceased. The mixture is then cooled to 40° C. and 40 g of methyl iodide are subsequently added dropwise thereto. Stirring and the temperature are then maintained until evolution ceases, after which the mixture is subjected to thin-layer chromatography. The solvent and the volatile products are then distilled off under reduced pressure and the residue is taken up in a minimum amount of dichloromethane. The solution obtained is filtered over 400 g of silica using as eluant a $CH_2Cl_2/CH_3OH$ mixture progressively concentrated to 5% $CH_3OH$.

Evaporation of the solvent yields 27 g of the expected compound in pure form, m.p.: 93° C.

EXAMPLE 15

5-Methoxy-2-(3,4-dimethoxyphenyl)-7-(2,3-dihydroxypropoxy)-4H-1-benzopyran-4-one

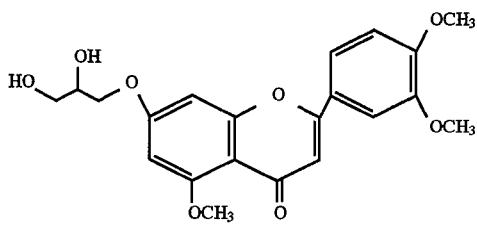

25 g of the compound of Example 14 are hydrolysed as described in Example 10 to yield, after recrystallisation from acetonitrile, 18 g of the expected compound in pure form, m.p.: 143° C.

EXAMPLE 16

(R,S)-5-Hydroxy-2-(3-hydroxy-4-methoxyphenyl)-7-(2,3-dihydroxypropoxy)-4H-1-benzopyran-4-one

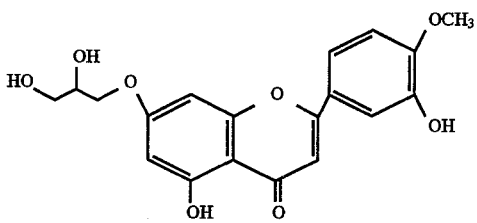

3 g of (R,S)-5-hydroxy-7-[(2,2-dimethyl-1,3-dioxol-4-yl)methoxy]-2-(3-hydroxy-4-methoxyphenyl)-4H-1-benzopyran-4-one, prepared in accordance with Example 4, are hydrolysed as described in Example 10 to yield, after recrystallisation from isopropanol, 2.5 g of the expected compound in pure form, m.p.: 219°–220° C.

EXAMPLES 17 AND 18

The compounds forming the subject of the following Examples were prepared by proceeding as described in Example 16:

17) (R)-5-Hydroxy-2-(3-hydroxy-4-methoxyphenyl)-7-(2,3-dihydroxypropoxy)-4H-1-benzopyran-4-one, m.p.: 228° C., starting from (S)-hydroxy-7-[(2,2-dimethyl-1,3-dioxol-4-yl)methoxy]-2-(3-hydroxy-4-methoxyphenyl)-4H-1-benzopyran-4-one, prepared in accordance with Example 6

Index of rotation [c]=1% in DMSO at 20° C.:
α(589 nm)=−9°
α(578 nm)=−9°
α(546 nm)=−9.6°.

18) (S)-5-Hydroxy-2-(3-hydroxy-4-methoxyphenyl)-7-(2,3-dihydroxypropoxy)-4H-1-benzopyran-4-one, m.p.: 228° C., starting from (R)-5-hydroxy-7-[(2,2-dimethyl-1,3-dioxol-4-yl)methoxy]-2-(3-hydroxy-4-methoxyphenyl)-4H-1-benzopyran-4-one, prepared in accordance with Example 5.

Index of rotation [c]=1% in DMSO at 20° C.:
α(589 nm)=+9°
α(578 nm)=+9°
α(546 nm)=+9.6°.

EXAMPLE 19

5,7-Di-[(2,2-dimethyl-1,3-dioxol-4-yl)methoxy]-2-(3-hydroxy-4-methoxyphenyl)-4H-1-benzopyran-4-one

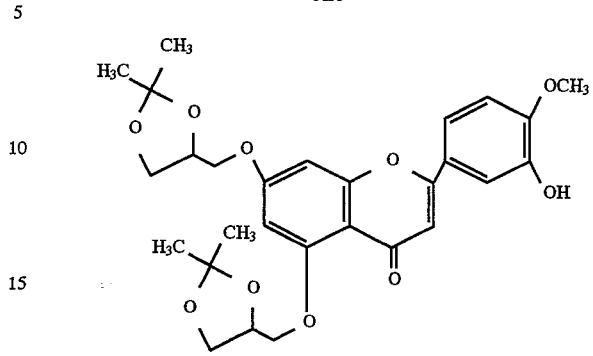

A) Step A
5-Hydroxy-7-[(2,2-dimethyldioxol-4-yl)methoxy]-2-(3-benzyloxy-4-methoxyphenyl)-4H-1-benzopyran-4-one.

10 g of (R,S)-5-hydroxy-7-[(2,2-dimethyldioxol-4-yl)methoxy]-2-(3-hydroxy-4-methoxyphenyl)-4H-1-benzopyran-4-one prepared in accordance with Example 4 and 5.7 g of potassium carbonate are stirred at reflux in 300 ml of acetone, then 5.8 g of benzyl bromide in 100 ml of acetone are slowly added. The reaction mixture is then maintained at reflux with stirring for 12 hours and subsequently cooled and filtered. The acetone is removed from the filtrate by distillation, and the resulting residue, which is 98% pure 5-hydroxy-7-[(2,2-dimethyldioxol-4-yl)methoxy]-2-(3-benzyloxy-4-methoxyphenyl)-4H-1-benzopyran-4-one, is used as it is. An analytical sample was prepared by recrystallisation from isopropanol, m.p.: 189°–191° C.

B) Step B
5,7-Di-[(2,2-dimethyl-1,3-dioxol-4-yl)methoxy]-2-(3-benzyloxy-4-methoxyphenyl)-4H-1-benzopyran-4-one.

8 g of the compound prepared in Step A of Example 19 are alkylated as described in Example 4 with (2,2-dimethyl-1,3-dioxol-4-yl)methyl p-toluenesulphonate, using sodium hydride as base, in dimethylformamide. 4.5 g of the expected product are obtained in the form of a mixture of diastereoisomers.

C) Step C
5,7-Di-[(2,2-dimethyl-1,3-dioxol-4-yl)methoxy]-2-(3-hydroxy-4-methoxyphenyl)4H-1-benzopyran-4-one.

4 g of the product obtained in Step B above are subjected to catalytic hydrogenolysis as described in Example 13 to yield, after work-up, approximately 3.2 g of the expected product in pure form. m.p.: 160° C.

EXAMPLE 20

5,7-Di-(2,3-dihydroxypropoxy)-2-(3-hydroxy-4-methoxyphenyl)-4H-1-benzopyran-4-one

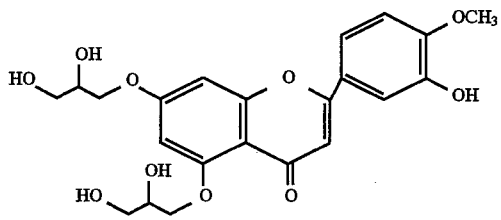

3 g of the compound of Example 19 are hydrolysed under the conditions described in Example 16, then treated by evaporation of the aqueous acetic medium under reduced pressure. The residue is dissolved in a minimum amount of methanol, filtered over Millipore and the filtrate is concentrated to dryness. The residue obtained is treated with 50 ml of boiling water and then the whole is cooled. The resulting precipitate is then stirred in the cold with 50 ml of diethyl ether to yield 1.8 g of the expected compound in pure form, m.p.: 204° C.

EXAMPLE 21

5-Hydroxy-7-[(2,2-dimethyl-1,3-dioxol-4-yl)methoxy]-2-(4-methoxy-3-pivaloyloxyphenyl)-4H-1-benzopyran-4-one

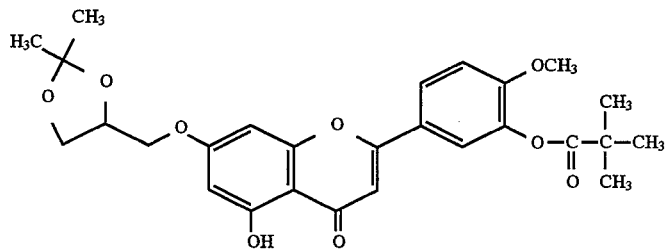

41 g of (R,S)-5-hydroxy-7-[(2,2-dimethyl-1,3-dioxol-4-yl)methoxy]-2-(3-hydroxy-4-methoxyphenyl)-4H-1-benzopyran-4-one, prepared in accordance with Example 4, are suspended in 1250 ml of dioxane and 10 g of triethylamine. The whole is cooled in an ice bath and then 12 g of pivaloyl chloride are added dropwise with stirring. Once the addition is complete, the reaction mixture is allowed to return to room temperature, then filtered. The filtrate is concentrated to dryness and the residue is recrystallised from acetonitrile, yielding 48 g of the expected compound, m.p.: 204°–205° C.

EXAMPLE 22

5-Hydroxy-7-[(2,2-dimethyl-1,3-dioxol-4-yl)methoxy]-2-(3-isopropylcarbonyloxy-4methoxyphenyl)-4H-1-benzopyran-4-one

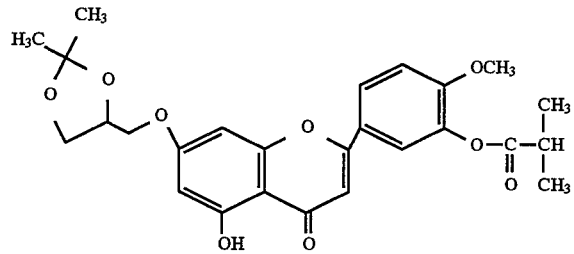

This compound was prepared as described in Example 21, but using isobutyryl chloride instead of pivaloyl chloride.

EXAMPLE 23

5-Hydroxy-2-[(4-methoxy-3-pivaloyloxyphenyl)-7-(2,3-dihydroxypropoxy)-4H-1-benzopyran-4-one

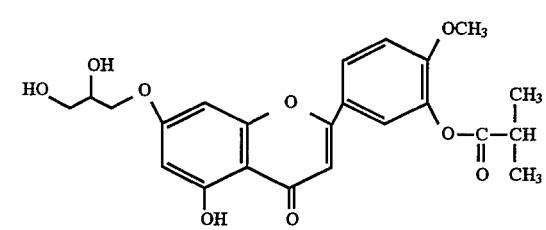

49.8 g of the compound forming the subject of Example 21 are progressively heated in a mixture of 300 ml of acetic acid and 300 ml of water. After the addition, the mixture is maintained at the same temperature for 5 minutes. After the addition of 300 ml of water, the mixture is brought to room temperature. The resulting precipitate is collected by filtration and then recrystallised from an acetone/dichloromethane mixture, yielding 35 g of the expected compound, m.p.: 130° C.

EXAMPLE 24

5-Hydroxy-2-(3-isopropylcarbonyloxy-4-methoxyphenyl)-7-(2,3-dihydroxypropoxy)-4H-1-benzopyran-4-one This compound, m.p.: 144°–145° C., was prepared as described in Example 23 starting from the compound forming the subject of Example 22.

EXAMPLE 25

5-Allyloxy-2-(3-allyloxy-4-methoxyphenyl)-7-[(2,2-dimethyl-1,3-dioxol-4-yl)methoxy]-4H-1-benzopyran-4-one

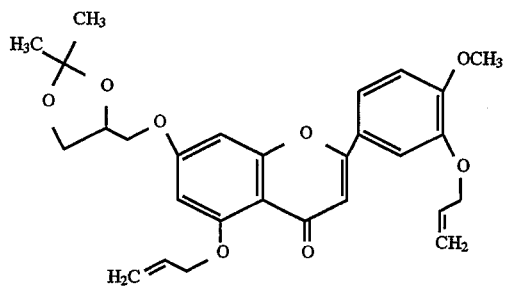

41 g of the compound forming the subject of Example 4 are alkylated with 32 g of allyl bromide and 8 g of sodium hydride as described in Example 3, thereby yielding, after recrystallisation from isopropanol, 32.8 g of the expected compound of 95% purity, which is used as it is. An analytical sample was prepared by recrystallisation twice from isopropanol, m.p.: 114° C.

EXAMPLE 26

5-Allyloxy-2-(3-allyloxy-4-methoxyphenyl)-7-[(2,3-dihydroxypropoxy)-4H-1-benzopyran-4-one

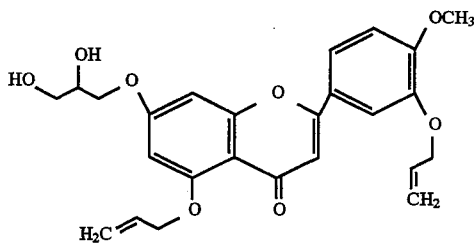

5 g of the compound forming the subject of Example 25 are hydrolysed as described in Example 10 to yield, after recrystallisation from isopropanol, 4.2 g of the expected compound, m.p.: 127° C.

EXAMPLE 27

6-Allyl-5-hydroxy-2-(2-allyl-3-hydroxy-4-methoxyphenyl)-7-[(2,2-dimethyl-1,3-dioxol-4-yl)methoxy]-4H-1-benzopyran-4-one

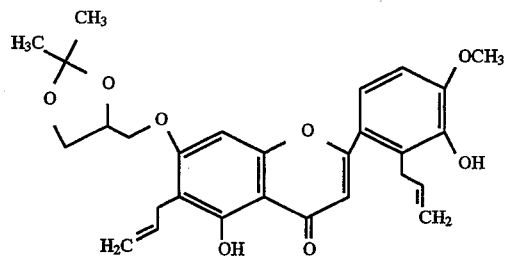

5 g of the compound forming the subject of Example 25 are treated as described in Example 11, Step B, to yield 4.8 g of the expected compound which is used as it is.

EXAMPLE 28

6-Allyl-5-hydroxy-2-(2-allyl-3-hydroxy-5-methoxyphenyl)-7-(2,3-dihydroxypropoxy)-4H-1-benzopyran-4-one

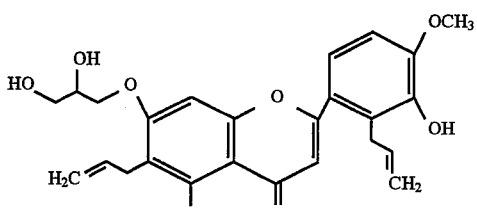

2.4 g of the compound forming the subject of Example 27 are hydrolysed to yield, after recrystallisation from an isopropanol/ether mixture, 1.8 g of the expected compound, m.p.: 123° C.

EXAMPLE 29

5-Hydroxy-7-[(2,2-dimethyl-1,3-dioxol-4-yl)methoxy]-2-(3-hydroxy-4-methoxy-2-propylphenyl)-6-propyl-4H-1-benzopyran-4-one

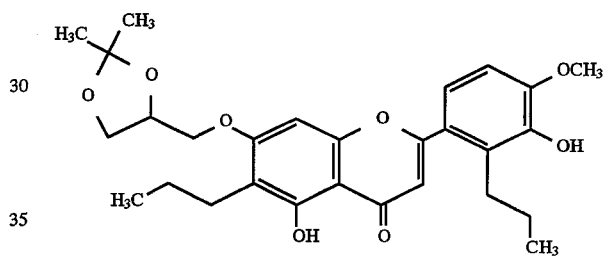

2.4 g of the compound of Example 27 are hydrogenated in 40 ml of dimethylformamide with 100 mg of catalyst (5% palladium-on-carbon) under a hydrogen pressure of 6300 hPa. After absorption of the theoretical amount of hydrogen, the mixture is filtered over Millipore and the filtrate is distilled under reduced pressure. The residue yields 2.4 g of the expected product which is used as it is. An analytical sample was prepared by recrystallisation from isopropanol, m.p. 148° C.

EXAMPLE 30

5-Hydroxy-2-(3-hydroxy-4-methoxy-2-propylphenyl)-6-propyl-7-(2,3-dihydroxypropoxy)-4H-1-benzopyran-4-one

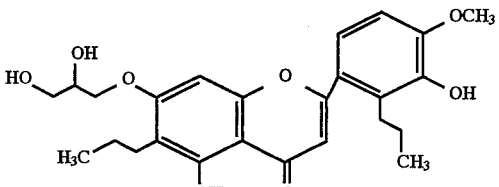

2.4 g of the compound forming the subject of Example 29 are hydrolysed as described in Example 10 to yield, after recrystallisation from a mixture of isopropanol and ether, 2 g of the expected compound, m.p.: 196° C.

EXAMPLE 31

5-Hydroxy-2-{[4-methoxy-3-(6-carboxy-3,4,5-trihydroxytetrahydropyran-2-yl)oxy]phenyl}-7-(2,3-dihydroxypropoxy)-4H-1-benzopyran-4-one

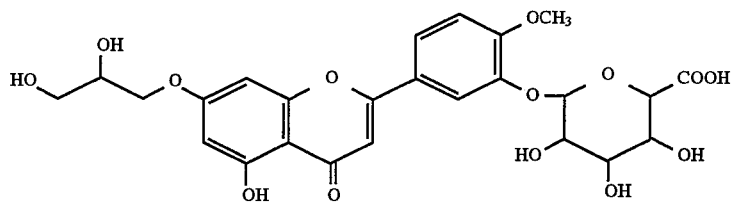

A) Step A

5-Hydroxy-7-[(2,2-dimethyl-1,3-dioxol-4-yl)methoxy]-2-{4-methoxy-[3-(6-methoxycarbonyl-3,4,5-triacetoxytetrahydropyran-2-yl)oxy]phenyl}-4H-1-benzopyran-4-one.

The coupling of the compound forming the subject of Example 4 and methyl tri-O-acetylglucuronate is carried out in accordance with the method described by G. T. Badman et al., J. Organmet. Chem. 338 (1–2), 117–121 (1990). Thus, 410 mg of the compound forming the subject of Example 4 are stirred for 48 hours with 165 mg of diethylazodicarboxylate and 500 mg of methyl tri-O-acetylglucuronate in 25 ml of tetrahydrofuran at room temperature and under an inert atmosphere, after which the solvent is removed under reduced pressure and the residue is chromatographed on 30 g of silica using a cyclohexane/ethyl acetate mixture (1/1) as eluant. 390 mg of the expected compound in the form of an oil are thereby obtained.

B) Step B

5-Hydroxy-2-{[4-methoxy-3-(6-carboxy-3,4,5-trihydroxytetrahydropyran-2-yl)oxy]phenyl}-7-(2,3-dihydroxypropoxy)-4H-1-benzopyran-4-one.

The hydrolysis of the compound obtained in Step A is carried out in accordance with the method described by Cheukk. Lav et. al., J. Med. Chem., 35, (7), 1299–1318 (1992). Thus, the oil obtained in Step A above is added to a mixture of 8 ml of normal sodium hydroxide solution and 12 ml of methanol. The whole is stirred at room temperature for approximately 4 hours, and the mixture is then treated with 8 ml of normal HCl and stirred at room temperature for 30 minutes, after which 1 ml of normal hydrochloric acid is added thereto and the whole is stirred for 30 minutes at 25° C. under an inert atmosphere. The solution is lyophilised and the residue is chromatographed on silica using as eluant an ethyl acetate/acetic acid mixture with a progressively increasing concentration of acetic acid. After evaporation of the solvent from the pure fractions, 250 mg of the expected compound in the form of an amorphous gum are obtained.

EXAMPLE 32

(R,S)-5-Hydroxy-7-[(2,2-dimethyl-1,3-dioxol-4-yl)methoxy]-2-(3-allyloxy-4-methoxyphenyl)-4H-1-benzopyran-4-one

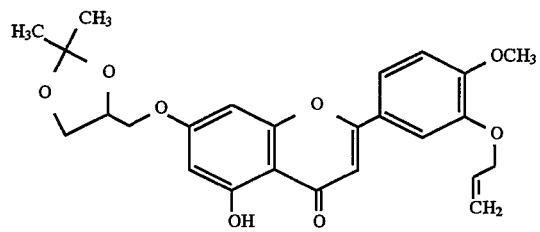

41 g of the compound forming the subject of Example 4 and 15 g of potassium carbonate are stirred in 500 ml of dimethylformamide at 90° C., and then 15 g of allyl bromide are added thereto. Heating is maintained for a further 2 hours after the addition, then the mixture is allowed to return to room temperature and subsequently filtered. The filtrate is concentrated to dryness with removal of the dimethylformamide by distillation. The residue obtained is taken up in 1000 ml of dichloromethane. After filtration, the filtrate is concentrated to dryness by removal of the dichloromethane by distillation, and the residue is recrystallised from isopropanol, yielding 36 g of the expected compound, m.p.: 139° C.

EXAMPLES 33 AND 34

The compounds forming the subject of the following two Examples were prepared by proceeding as described in Example 32:

33) (R)-5-Hydroxy-7-[(2,2-dimethyl-1,3-dioxol-4-yl)methoxy]-2-(3-allyloxy-4-methoxyphenyl)-4H-1-benzopyran-4-one, starting from the compound forming the subject of Example 5.

34) (S)-5-Hydroxy-7-[(2,2-dimethyl-1,3-dioxol-4-yl)methoxy]-2-(3-allyloxy-4-methoxyphenyl)-4H-1-benzopyran-4-one, starting from the compound forming the subject of Example 6.

EXAMPLE 35

5-Hydroxy-7-[(2,2-dimethyl-1,3-dioxol-4-yl)methoxy]-2-(4-methoxy-3-propoxyphenyl)-4H-1-benzopyran-4-one

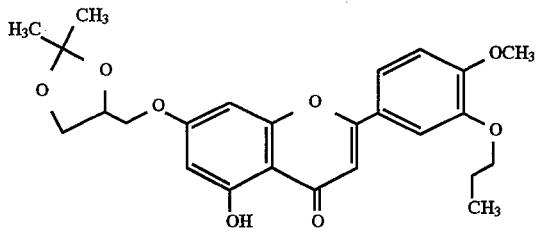

4.5 g of the compound forming the subject of Example 32 were hydrogenated as described in Example 29 to yield 4.5 g of the expected compound, which can be used as it is.

EXAMPLE 36

5-Hydroxy-2-(4-methoxy-3-propoxyphenyl)-7-(2,3-dihydroxypropoxy)-4H-1-benzopyran-4-one

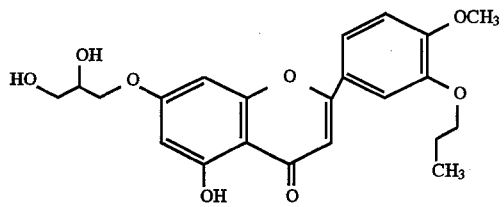

4.5 g of the compound forming the subject of Example 35 were hydrolysed as described in Example 10 to yield, after recrystallisation from an isopropanol/ether mixture, 3.8 g of the expected compound. m.p.: 157° C.

EXAMPLE 37

(R,S)-5-Hydroxy-7-[2,2-dimethyl-1,3-dioxol-4-yl)methoxy]-2-(2-allyl-3-hydroxy-4-methoxyphenyl)-4H-1-benzopyran-4-one

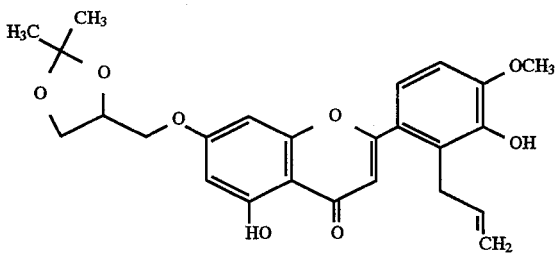

45.4 g of the compound forming the subject of Example 32 were treated as described in Example 11, Step B, and then recrystallised from isopropanol, yielding 43 g of the expected compound.

EXAMPLES 38–39

The compounds forming the subject of the following two Examples were prepared by proceeding as described in Example 37:

38) (R)-5-hydroxy-7-[(2,2-dimethyl-1,3-dioxol-4-yl)methoxy]-2-(2-allyl-3-hydroxy-4-methoxyphenyl)-4H-1-benzopyran-4-one, starting from the compound forming the subject of Example 33.

39) (S)- 5-hydroxy-7-[(2,2-dimethyl-1,3-dioxol-4-yl)methoxy]-2-(2-allyl-3-hydroxy-4-methoxyphenyl)-4H-1-benzopyran-4-one, starting from the compound forming the subject of Example 34.

EXAMPLE 40

(R,S)-5-Hydroxy-2-(2-allyl-3-hydroxy-4-methoxyphenyl)-7-(2,3-dihydroxypropoxy)-4H-1-benzopyran-4-one

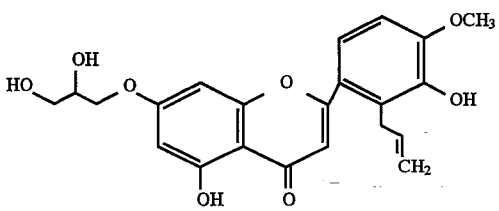

45.4 g of the compound forming the subject of Example 37 were added to a mixture of 300 ml of water and 300 ml of acetic acid.

The whole was progressively heated until dissolution was complete, then for a further 5 minutes after dissolution. After the addition of 200 ml of water and returning to room temperature, the precipitate obtained was filtered and then recrystallised from isopropanol, finally yielding 35.5 g of the expected compound, m.p.: 134° C.

EXAMPLE 41–42

The compounds forming the subject of the following two Examples were prepared by proceeding as described in Example 40:

41) (R)-5-Hydroxy-2-(2-allyl-3-hydroxy-4-methoxyphenyl)-7-(2,3-dihydroxypropoxy)-4H-1-benzopyran-4-one, m.p.: 164° C., starting from the compound forming the subject of Example 39.

Index of rotation [c]=1% in dimethylformamide:

α(589 nm)=−6.7°

α(578 nm)=−7.0°

α(546 nm)=−7.9°.

42) (S)-5-Hydroxy-2-(2-allyl-3-hydroxy-4-methoxyphenyl)-7-(2,3-dihydroxypropoxy)-4H-1-benzopyran-4-one, m.p.: 164° C., starting from the compound forming the subject of Example 38.

Index of rotation [c]=1% in dimethylformamide:

α(589 nm)=+6.7°

α(578 nm)=+7.0°

α(546 nm)=+7.9°.

EXAMPLE 43

(R,S)-5-Hydroxy-7-[(2,2-dimethyl-1,3-dioxol-4-yl) methoxy]-2-(3-hydroxy-4-methoxy-2-propylphenyl)-4H-1-benzopyran-4-one

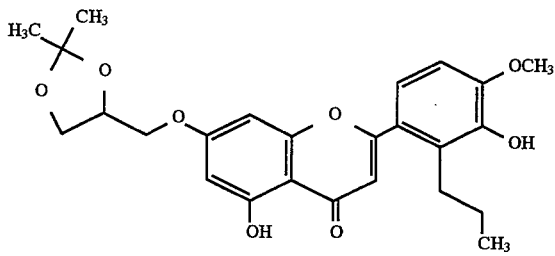

45.4 g of the compound forming the subject of Example 37 are dissolved, with the application of heat, in 800 ml of 96% ethanol. The mixture is hydrogenated under a hydrogen pressure of 6300 hPa in the presence of 2 g of 5% palladium-on-carbon. After the absorption of the stoichiometric amount of hydrogen, the reaction mixture is filtered and the filtrate is concentrated to dryness by removing the ethanol by distillation under reduced pressure, yielding 45 g of the expected compound, m.p.: 121° C.

EXAMPLES 44–45

The compounds forming the subject of the following two Examples were prepared by proceeding as described in Example 43:

44) (R)-5-Hydroxy-7-[(2,2-dimethyl-1,3-dioxol-4-yl)methoxy]-2-(3-hydroxy-4-methoxy-2-propylphenyl)-4H-1-benzopyran-4-one, starting from the compound forming the subject of Example 38.

45) (S)-5-Hydroxy-7-[(2,2-dimethyl-1,3-dioxol-4-yl) methoxy]-2-(3-hydroxy-4-methoxy-2-propylphenyl)-4H-1-benzopyran-4-one, starting from the compound forming the subject of Example 39.

EXAMPLE 46

(R,S)-5-Hydroxy-2-(3-hydroxy-4-methoxy-2-propylphenyl)-7-(2,3-dihydroxypropoxy)-4H-1-benzopyran-4-one

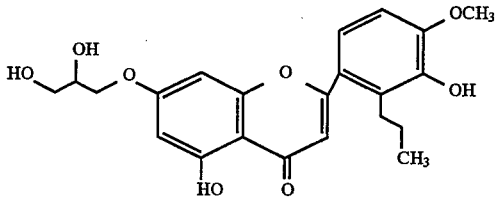

45.6 g of the compound forming the subject of Example 43 are added to a mixture of 300 ml of water and 300 ml of acetic acid. The whole is progressively heated until dissolution is complete, after which heating is continued for a further 5 minutes and then 200 ml of water are added.

After returning to room temperature, the resulting precipitate is filtered, washed with water and then recrystallised from isopropanol to yield the expected racemic compound which exists in the following different crystalline forms:

the α form (m.p.: 145° C., ν CO (IR): 1672 cm$^{-1}$) obtained by dissolving 40 g of the crude product in 600 ml of isopropanol at the boil, then allowing slowly to return to room temperature and to crystallise for one week without stirring;

the β form (m.p.: 156° C., ν CO (IR): 1658 cm$^{-1}$) obtained by dissolving 40 g of the crude product in 200 ml of isopropanol at the boil and then rapidly cooling with stirring;

the γ form (m.p.: 121°–3° C., ν CO (IR): 1668 cm$^{-1}$) obtained by recrystallising 40 g of the crude product in 400 ml of anhydrous methanol.

EXAMPLES 47–48

The compounds forming the subject of the following two Examples were prepared by proceeding as described in Example 46:

47) (R)-5-Hydroxy-2-(3-hydroxy-4-methoxy-2-propylphenyl)-7-(2,3-dihydroxypropoxy)-4H-1-benzopyran-4-one, m.p. 159° C., starting from the compound forming the subject of Example 45.

Index of rotation [c]=0.5% in CH$_3$OH:
α(589 nm)=−7.1°
α(578 nm)=−7.6°
α(546 nm)=−8.7°.

48) (S)-5-Hydroxy-2-(3-hydroxy-4-methoxy-2-propylphenyl)-7-(2,3-dihydroxypropoxy)-4H-1-benzopyran-4-one, m.p.: 159° C., starting from the compound forming the subject of Example 44.

Index of rotation [c]=0.5% in CH$_3$OH:
α(589 nm)=+7.1°
α(578 nm)=+7.6°
α(546 nm)=+8.7°.

EXAMPLE 49

(R,S)-5-Hydroxy-2-(3-hydroxy-4-methoxy-2-propylphenyl)-7-(3-acetoxy-2-hydroxypropoxy)-4H-1-benzopyran-4-one

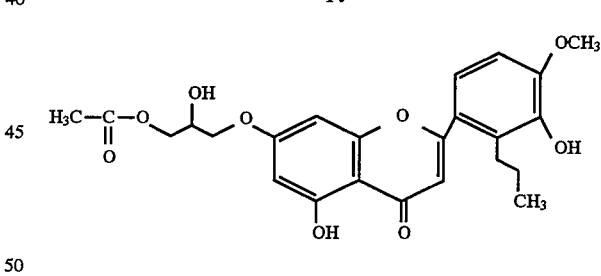

This racemic compound, m.p.: 147°–148° C., was obtained by esterification of the compound forming the subject of Example 46.

EXAMPLES 50–51

The compounds forming the subject of the following two Examples were prepared analogously to Example 49:

50) (R)-5-Hydroxy-2-(3-hydroxy-4-methoxy-2-propylphenyl)-7-(3-acetoxy-2-hydroxypropoxy)-4H-1-benzopyran4-one, m.p.: 140° C., starting from the compound forming the subject of Example 48.

51) (S)-5-Hydroxy-2-(3-hydroxy-4-methoxy-2-propylphenyl)-7-(3-acetoxy-2-hydroxypropoxy)-4H-1-benzopyran-4-one, m.p.: 140° C., starting from the compound forming the subject of Example 47.

EXAMPLE 52

(R,S)-5-tert-Butylcarbonyloxy-7-[(2,2-dimethyl-1,3-dioxol-4-yl)methoxy]-2-(3-hydroxy-4-methoxy-2-propylphenyl)-4H-1-benzopyran-4-one

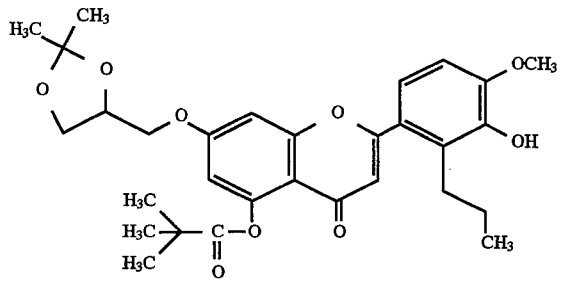

4.56 g of the compound forming the subject of Example 43 are dissolved in 100 ml of dioxane and 1 g of triethylamine. The solution is cooled on an ice bath and then 1.2 g of pivaloyl chloride are added dropwise. After returning to room temperature, then heating at reflux with stirring for 48 hours, the mixture is allowed to return to room temperature and the resulting precipitate is filtered. The filtrate is concentrated to dryness by distilling off the dioxane under reduced pressure, and the residue obtained is taken up in 50 ml of diethyl ether. Vigorous stirring until a fine precipitate is obtained allows 2.7 g of the expected compound to be obtained.

EXAMPLE 53

(R,S)-5-tert-Butylcarbonyloxy-2-(3-hydroxy-4-methoxy-2-propylphenyl)-7-(2,3-dihydroxypropoxy)-4H-1-benzopyran-4-one

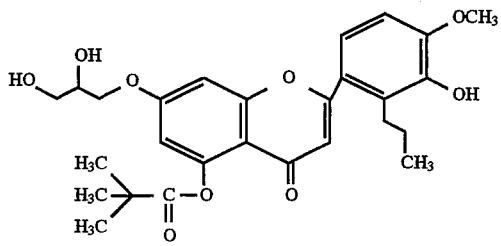

5.4 g of the compound forming the subject of Example 52 are added to a mixture of 30 ml of water and 30 ml of acetic acid. The whole is progressively heated until dissolution is complete. After returning to room temperature, 20 ml of water are added and the resulting gummy precipitate is collected by removing the supernatant. The gum is dissolved in dichloromethane and the resulting solution is dried over magnesium sulphate. The solvent is removed under reduced pressure and the residue is recrystallised from anhydrous diethyl ether, yielding 3.6 g of the expected compound, m.p.: 158° C.

EXAMPLE 54

5-Methoxy-7-[(2,2-dimethyl-1,3-dioxol-4-yl)methoxy]-2-(3-allyloxy-4-methoxyphenyl)-4H-1-benzopyran-4-one

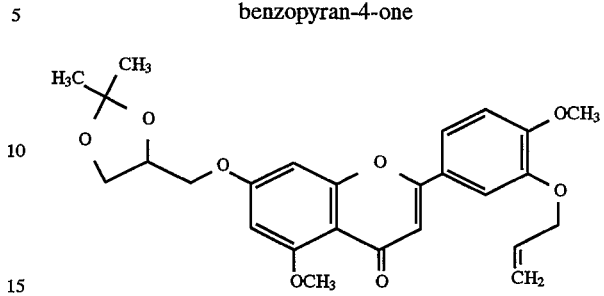

4.5 g of the compound forming the subject of Example 32 are methylated under the conditions described in Example 14 using 2 g of potassium carbonate and 2 g of methyl iodide to yield, after treatment, 3.7 g of the expected compound, which can be used as it is. An analytical sample was prepared by recrystallisation from ethyl acetate, m.p.: 156° C.

EXAMPLE 55

5-Methoxy-7-[(2,2-dimethyl-1,3-dioxol-4-yl)methoxy]-2-(2-allyl-3-hydroxy-4-methoxyphenyl)-4H-1-benzopyran-4-one

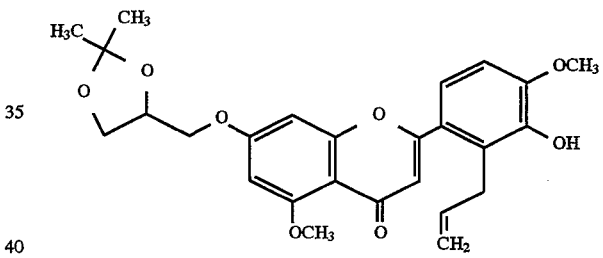

3.5 g of the compound forming the subject of Example 54 are transposed as described in Example 11, Step B, to yield 3.5 g of the expected compound which can be used as it is.

EXAMPLE 56

5-Methoxy-7-[(2,2-dimethyl-1,3-dioxol-4-yl)methoxy]-2-(3-hydroxy-4-methoxy-2-propylphenyl)-4H-1-benzopyran-4-one

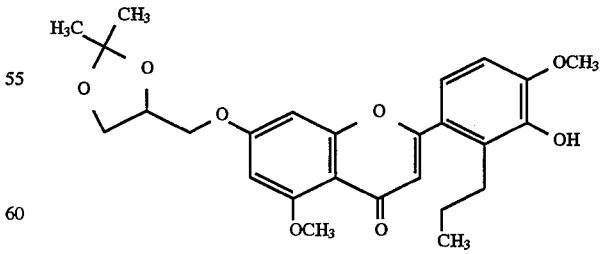

3.5 g of the compound forming the subject of Example 55 are hydrogenated under the conditions described in Example 29 to yield approximately 3.5 g of the expected compound which can be used as it is.

EXAMPLE 57

5-Methoxy-2-(3-hydroxy-4-methoxy-2-propylphenyl)-7-(2,3-dihydroxypropoxy)-4H-1-benzopyran-4-one

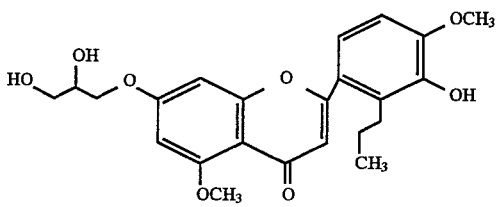

3.5 g of the compound forming the subject of Example 56 are hydrolysed as described in Example 10 to yield approximately 2.7 g of the expected compound.

EXAMPLE 58

5-Hydroxy-2-[4-methoxy-2-propyl-3-(6-carboxy-3,4,5-trihydroxytetrahydropyran-2-yloxy)phenyl]-7-(2,3-dihydroxypropoxy)-4 H-1-benzopyran-4-one

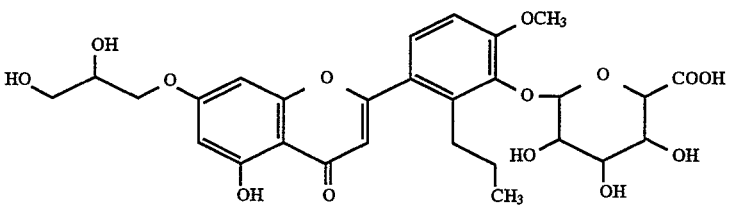

A) Step A
5-Methoxy-7-[(2,2-dimethyl-1,3-dioxol-4-yl)methoxy]-2-[4-methoxy-2-propyl-3-(6-methoxycarbonyl-3,4,5-triacetoxytetrahydropyran-2-yloxy)phenyl]-4H-1-benzopyran-4-one.

This compound was obtained starting from the compound forming the subject of Example 43 by proceeding as described in Example 31, Step A.

B) Step B
5-Hydroxy-2-[4-methoxy-2-propyl-3-(6-carboxy-3,4,5-trihydroxytetrahydropyran-2-yloxy)phenyl]-7-(2,3-dihydroxypropoxy)-4H-1-benzopyran-4-one.

This amorphous compound was obtained starting from the compound prepared above in Step A, by proceeding as described in Example 31, Step B.

EXAMPLE 59

5-Hydroxy-2-[4-methoxy-3-(2,3-dihydroxypropoxy)phenyl]-7-(2,3-dihydroxypropoxy)-4H-1-benzopyran-4-one

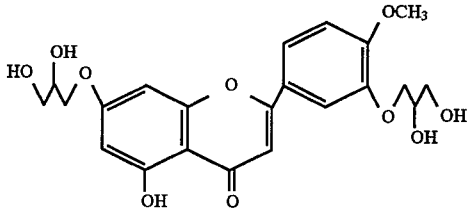

1g of the compound forming the subject of Example 7 is hydrolysed under the conditions described in Example 16 to yield, after recrystallisation from isopropanol, 0.6 g of the expected compound,: 166° C.

EXAMPLE 60

2-[4-Methoxy-3-(2,3-dihydroxypropoxy)phenyl]-5,7-(2,3-dihydroxypropoxy)-4H-1-benzopyran-4-one

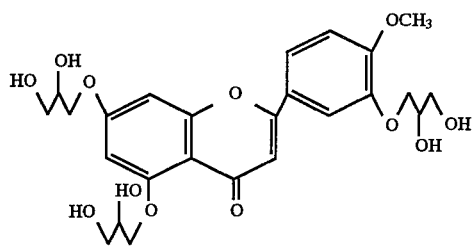

3 g of the compound forming the subject of Example 8 are treated under the conditions described in Example 20 except that the residue was not taken up in boiling water. After recrystallisation from ether, approximately 1.4 g of the expected compound were obtained,
m.p.: 117°–120° C.

EXAMPLE 61

6-Allyl-5,7-dihydroxy-2-(3-hydroxy-4-methoxyphenyl)-4H-1-benzopyran-4-one

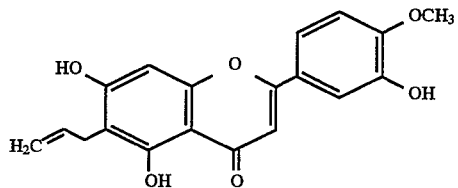

7 g of the compound forming the subject of Example 1 are transposed under the conditions described in Example 11, Step B. The mixture obtained after removal of the solvent is chromatographed on silica using a $CH_2Cl_2/CH_3COOC_2H_5$ mixture (90/10) as eluant. After combining identical fractions and removing the solvents by distillation the following are obtained:

2.6 g of the expected compound forming the subject of this Example and 4 g of the compound forming the subject of Example 62 below, it being possible for each of the compounds to be used as it is. By recrystallisation of each of the two compounds from isopropanol, analytical samples in pure form were obtained of the compounds forming the subject of:

Example 61, m.p.: 238° C., and
Example 62, m.p.: 255° C.

EXAMPLE 62

8-Allyl-5,7-dihydroxy-2-(3-hydroxy-4-methoxyphenyl)-4H-1-benzopyran-4-one

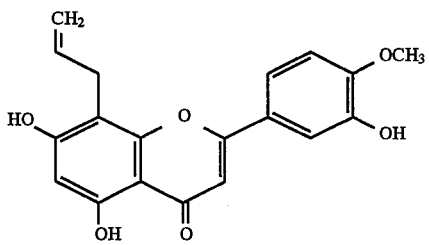

This compound was prepared as described in Example 61 above.

EXAMPLE 63

5,7-Dihydroxy-2-(3-hydroxy-4- methoxyphenyl)-6-propyl-4H-1-benzopyran-4-one

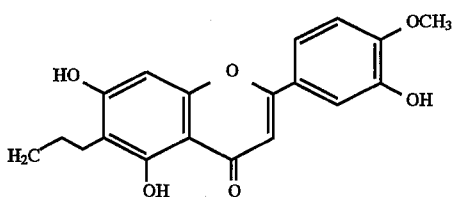

2.5 g of the compound forming the subject of Example 61 were hydrogenated under the conditions described in Example 29 to yield, after recrystallisation from isopropanol, approximately 2 g of the expected compound, m.p.: 232° C.

EXAMPLE 64

5,7-Dihydroxy-2-(3-hydroxy-4-methoxyphenyl)-8-propyl-4H-1-benzopyran-4-one

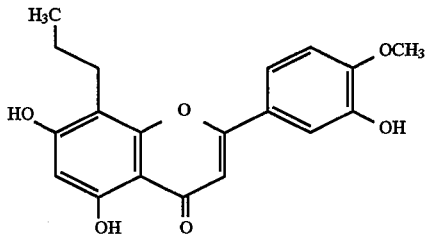

3.3 g of the compound forming the subject of Example 62, dissolved in 20 ml of dimethylformamide, are hydrogenated under a pressure of 6300 hPa in the presence of 100 mg of 5% palladium-on-carbon as catalyst. After absorption of the theoretical amount of hydrogen, the mixture is concentrated to dryness, the residue is taken up in ethanol with the application of heat and the solution is filtered over Millipore. The solvent is distilled off under reduced pressure and the residue is recrystallised from isopropanol to yield 3 g of the expected product, m.p.: 250° C.

EXAMPLE 65

8-Allyl-5,7-dihydroxy-2-(2-allyl-3-hydroxy-4-methoxyphenyl)-4H-1-benzopyran-4-one

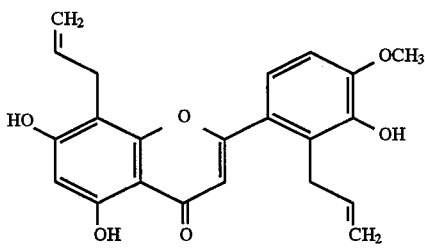

7.5 g of the compound forming the subject of Example 2 are transposed under the conditions described in Example 11, Step B. After removal of the solvent, the residue is chromatographed on silica using a $CH_2Cl_2/CH_3COOC_2H_5$ mixture (90/10) as eluant, to yield, after combining identical fractions and distilling off the solvents:

approximately 2.2 g of the expected compound forming the subject of this Example, and 3.8 g of the compound forming the subject of Example 66 below, it being possible for each of the compounds to be used as it is.

By recrystallisation of each of the two compounds from isopropanol, analytical samples in pure form were obtained of the compounds forming the subject of Example 66, m.p.: 224° C., and of Example 65 in the α form, m.p.: 120° C. (isopropanol), and in the 13 form, m.p.: 205° C. ($CH_2Cl_2$/$CH_3OH$).

EXAMPLE 66

6-Allyl-5,7-dihydroxy-2-(2-allyl-3-hydroxy-4-methoxyphenyl)-4H-1-benzopyran-4-one

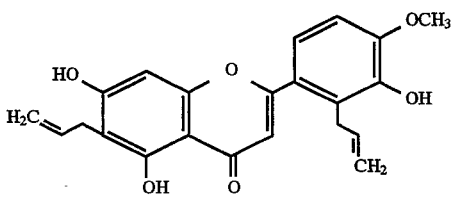

This compound was prepared as described in Example 65 above, m.p.: 224° C.

EXAMPLE 67

5,7-Dihydroxy-2-(3-hydroxy-4-methoxy-2-propylphenyl)-6-propyl-4H-1-benzopyran-4-one

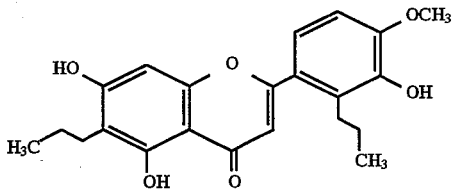

2 g of the compound forming the subject of Example 66 are hydrogenated under the conditions described in Example 29 to yield, after recrystallisation from an ether/petroleum ether mixture, 1.8 g of the expected compound, m.p.: 246° C.

EXAMPLE 68

5,7-Dihydroxy-2-(3-hydroxy-4-methoxy-2-propylphenyl)-8-propyl-4H-1-benzopyran-4-one

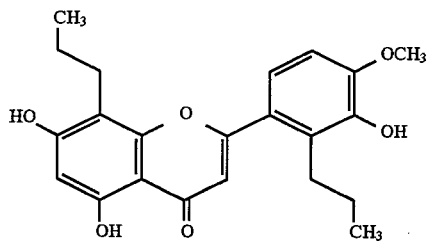

3.7 g of the compound forming the subject of Example 65 are hydrogenated under the conditions described in Example 29 to yield 3 g of the expected compound, m.p.: 134° C.

EXAMPLE 69

6,8-Diallyl-5,7-dihydroxy-2-(2-allyl-3-hydroxy-4-methoxyphenyl)-4H-1-benzopyran-4-one

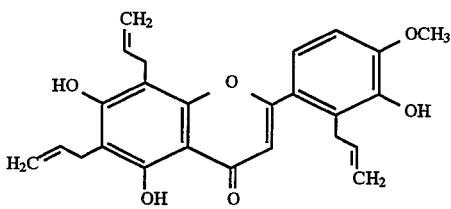

4.2 g of the compound forming the subject of Example 3 are transposed under the conditions described in Example 11, Step B. The residue is dissolved in $CH_2Cl_2$ and the solution is filtered over 10 g of silica using a $CH_2Cl_2$/$CH_3COOC_2H_5$ mixture (90/10) as eluant.

After recovery of the filtrate, the solvents are removed by distillation and the residue is recrystallised from an ethanol/ether mixture to yield, finally, 3.8 g of the expected compound, m.p.: 122°–123° C.

EXAMPLE 70

5,7-Dihydroxy-2-(3-hydroxy-4-methoxy-2-propylphenyl)-6,8-dipropyl-4H-1-benezopyran-4-one

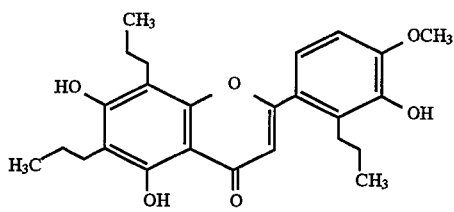

3.5 g of the compound forming the subject of Example 69 are hydrogenated under the conditions described in Example 29, using ethanol as solvent. After filtration over Millipore, removal of the solvent and crystallisation of the product from an ether/petroleum ether mixture, 3.3 g of the expected compound were obtained, m.p.: 170° C.

EXAMPLE 71

5,7-Dihydroxy-2-(3-allyloxy-4-methoxyphenyl)-4H-1-benzopyran-4-one

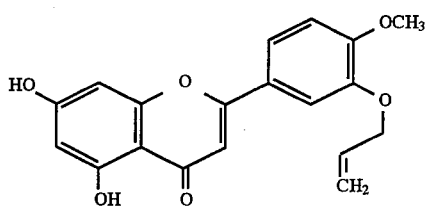

20 g of diosmetin are dissolved in a mixture of 400 ml of anhydrous methanol and 13.3 g of potassium pellets. The reaction mixture is maintained at room temperature and then 16 g of allyl bromide dissolved in 40 ml of methanol are added dropwise with stirring. Stirring is then continued for 48 hours, and the solvents and volatile products are subsequently distilled off under reduced pressure at room temperature. The residue is taken up in 400 ml of $CH_2Cl_2$, and the insoluble material is collected by filtration and then recrystallised from 440 ml of isopropanol to yield 19 g of the expected compound, m.p.: 219° C.

EXAMPLE 72

5,7-Dihydroxy-2-(2-allyl-3-hydroxy-4-methoxyphenyl)-4H-1-benzopyran-4-one

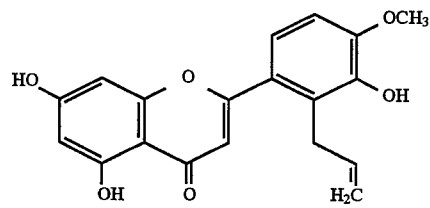

9 g of the compound forming the subject of Example 71 are transposed under the conditions described in Example 11, Step B, to obtain after recrystallisation from isopropanol, 7 g of the expected compound, m.p.: 234° C.

EXAMPLE 73

7-Allyloxy-5-hydroxy-2-(2-allyl-3-hydroxy-4-methoxyphenyl)-4H-1-benzopyran-4-one

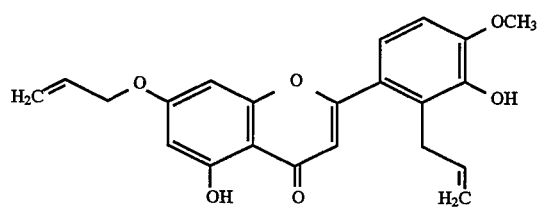

3.5 g of the compound forming the subject of Example 72 are alkylated with allyl bromide under the conditions described in Example 1 to yield, after recrystallisation from an isopropanol/ether mixture, 3.5 g of the expected compound, m.p.: 155° C.

EXAMPLE 74

5-Hydroxy-2-(3-hydroxy-4-methoxy-2-propylphenyl)-7-propoxy-4H-1-benzopyran-4-one

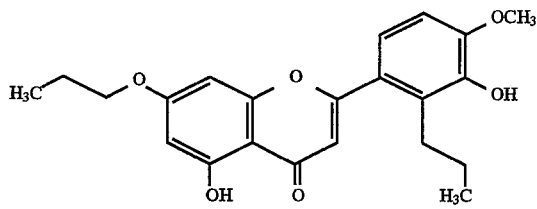

3.5 g of the compound forming the subject of Example 73 are catalytically reduced under the conditions described in Example 43 to yield, after recrystallisation from an isopropanol/ether mixture, 2.8 g of the expected compound, m.p.: 148°–149° C.

EXAMPLE 75

5-Hydroxy-7-[(2,2-dimethyl-1,3-dioxol-4-yl)methoxy]-2-(3-allyloxy-4-methoxyphenyl)-4H-1-benzopyran-4-one

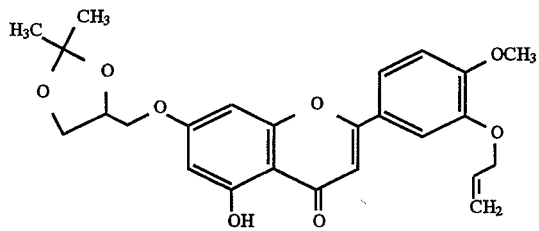

9g of the compound forming the subject of Example 71 are alkylated with (R,S)-(2,2-dimethylol-1,3-dioxol-4-yl) methyl p-toluenesulphonate under the conditions described in Example 4 to yield, finally, 9.1 g of the expected compound, m.p.: 139° C., which compound also formed the subject of Example 32.

EXAMPLE 76

5,7-Dihydroxy-2-(3-hydroxy-4-methoxy-2-propylphenyl)-4H-1-benzopyran-4-one

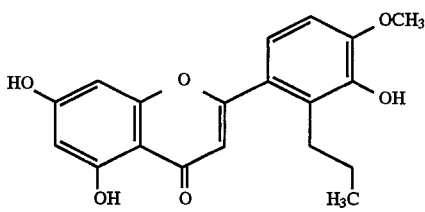

3.5 g of the compound forming the subject of Example 72 are hydrogenated under the conditions described in Example 43 to yield, after recrystallisation from isopropanol, 3.1 g of the expected compound, m.p.: 200° C.

This compound is identical to that prepared in accordance with Example 11.

EXAMPLE 77

6-Allyl-5,7-diallyloxy-2-(3-allyloxy-4-methoxyphenyl)-4H-1-benzopyran-4-one

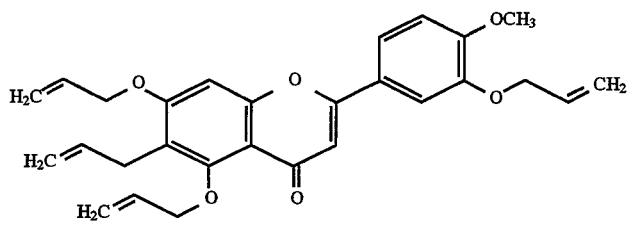

12 g of diosmetin in 100 ml of dimethylformamide and 15 ml of HMPA are added very slowly to a suspension of 4.8 g of sodium hydride in 30 ml of dimethylformamide. The mixture is then stirred at 40° C. until the evolution of gas has ceased. 17.25 g of allyl bromide are then added dropwise and the whole is heated at 60° C. for 16 hours, after which the solvents are removed by distillation under reduced pressure. The residue is taken up in dichloromethane and then chromatographed on silica using a 98% dichloromethane/2% methanol mixture as eluant. In that manner a fraction of 7.6 g of compound very fluorescent under 366 nm is recovered. An analytical sample of the title compound is prepared by recrystallisation from isopropanol, m.p.: 107° C.

EXAMPLE 78

7-Allyloxy 6,8-diallyl-2-(2-allyl-3-hydroxy-4-methoxyphenyl)-4H-1-benzopyran-4-one

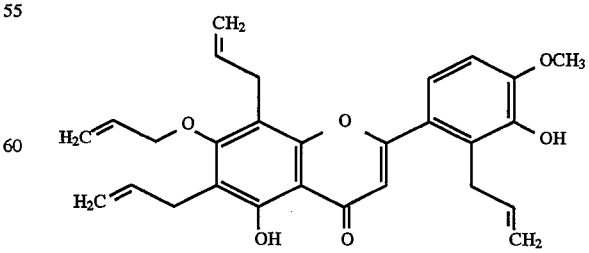

20 g of the compound forming the subject of Example 77 are transposed under the conditions of Example 11, Step B, with heating being maintained for 1 hour. After recrystallisation twice from an isopropanol/diethyl ether mixture, 9.8 g of the expected compound are recovered, m.p.: 125° C.

EXAMPLE 79

5,7-bis[(2,2-Dimethyldioxol-4-yl)methoxy]-2-(3-allyloxy-4-methoxyphenyl)-4H-1-benzopyran-4-one

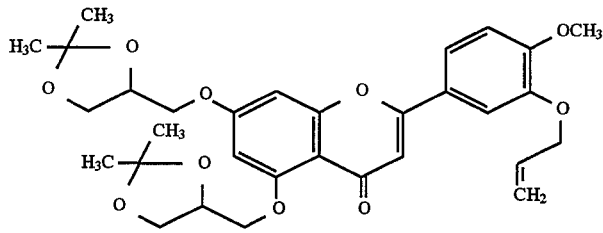

4 g of the compound forming the subject of Example 32 are alkylated with (2,2-dimethyl-1,3-dioxol-4-yl)methyl p-toluenesulphonate under the conditions of Example 19, Step B, yielding 3.6 g of the expected compound, m.p.: 123° C.

EXAMPLE 80

5,7-bis[(2,2-Dimethyldioxol-4-yl)methoxy]-2-(2-allyl-3-hydroxy-4-methoxyphenyl)-4H-1-benzopyran-4-one

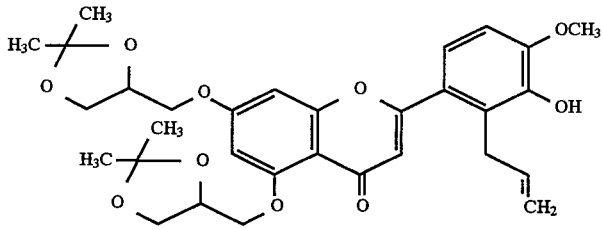

The compound forming the subject of Example 79 is transposed under the conditions of Example 11, Step B, yielding the title compound which can be used as it is. An analytical sample of that compound is prepared by recrystallisation from isopropanol, m.p.: 98°–100° C.

EXAMPLE 81

5,7-bis[(2,2-Dimethyldioxol-4-yl)methoxy]-2-(3-hydroxy-4-methoxy-2-n-propylphenyl)-4H-1-benzopyran4-one

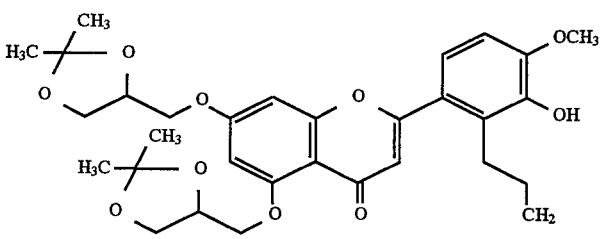

The compound forming the subject of Example 80 is hydrogenated under the conditions of Example 43 to yield the expected compound which can be used as it is.

EXAMPLE 82

5,7-bis(2,3-Dihydroxypropoxy)-2-(3-hydroxy-4-methoxy-2-propylphenyl)-4H-1-benzopyran-4-one

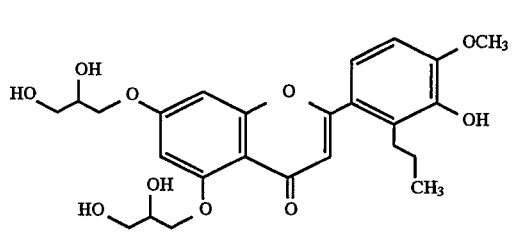

The compound forming the subject of Example 81 is hydrolysed under the conditions of Example 16. The title product obtained is recrystallised from a mixture of isopropanol, ether and petroleum ether, m.p.: 183°–188° C.

EXAMPLE 83

5-Methoxy-7-[(2,2-dimethyldioxol-4-yl)methoxy]-2-(3,4-dimethoxy-2-propylphenyl)-4H-1-benzopyran-4-one

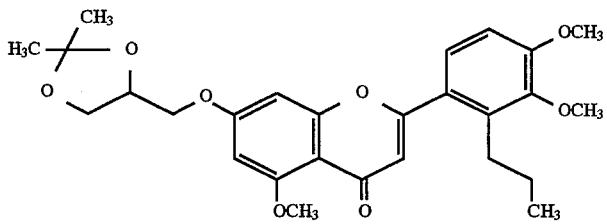

The compound forming the subject of Example 43 is alkylated under the conditions of Example 14 using sodium hydride. The title compound obtained is purified by recrystallisation from a mixture of cyclohexane and ethyl acetate, m.p.: 205° C. (dec.).

EXAMPLE 84

5-Methoxy-7-(2,3-dihydroxypropoxy)-2-(3,4-dimethoxy-2-n-propylphenyl)4H-1-benzopyran-4-one

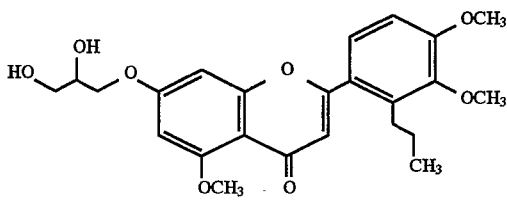

The compound forming the subject of Example 83 is hydrolysed under the conditions of Example 10 to yield the title compound, m.p.: 221° C.

EXAMPLE 85

5,7-bis-Propargyloxy-2-(4-methoxy-3-propargyloxyphenyl)-4H-1-benzopyran-4-one

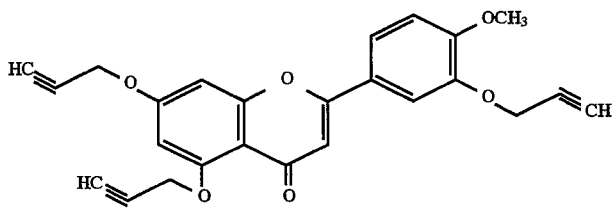

30 g of diosmetin are alkylated with propargyl bromide under the conditions of Example 3 to yield, after recrystallisation from isopropanol, 32 g of the title compound in pure form, m.p.: 196° C.

EXAMPLE 86

5,7-Dihydroxy-6,8-bis(1,2-dideuteroallyl)-2-[(4-methoxy-3-hydroxy-2-(1,2-dideuteroallyl)phenyl]-4H-1-benzopyran-4-one

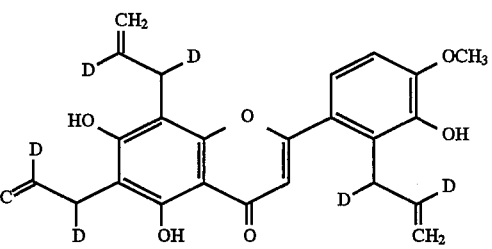

Step A—Deuteration 4 g of the compound of Example 85 are dissolved in 60 ml of dimethylformamide and then reduced with gaseous deuterium at atmospheric pressure in the presence of 0.7 g of Lindlar catalyst. After the absorption of 810 ml (125%) of deuterium, the solvent is removed by distillation under reduced pressure; the oily residue is filtered over 80 g of silica using a 99.5% dichloromethane/0.5% methanol mixture as eluant. 3.4 g of hexadeuterated compound (purity>90%), which is used as it is in the subsequent Step, are obtained.

Step B—Transposition

The compound obtained in Step A is heated to reflux under nitrogen in 34 ml of trichlorobenzene. The solvent is then distilled off under reduced pressure and the residue is chromatographed on 90 g of silica using a 95% toluene/5% ethyl acetate mixture as eluant. The product obtained after combining the pure fractions is then recrystallised from isopropanol to yield 2 g of the title product in pure form, m.p.: 128° C.

EXAMPLE 87

PHARMACOLOGICAL STUDY

1/Anti-hyperpermeability activity

The activity was determined by the effect of the compounds of the invention on the extravasation of FITC-dextran in the microcirculation of the hamster cheek pouch. The hamster cheek pouch is an experimental model allowing the quantitative study of the permeability of macromolecules using dextran labelled with fluorescein (FITC-dextran).

The experiments were carried out on male hamsters weighing from 85 to 120 g. The animals are anaesthetised with sodium pentobarbital (60 mg/kg, i.p.). During the experiment, the anaesthesia is maintained using α-chloralose (100 mg/kg) introduced through a catheter into the femoral artery. The animals breathe spontaneously through a tracheal canula and the body temperature is maintained at 37.5° C. using a "heating pad" controlled by a rectal thermistor.

After the initial anaesthesia, the cheek pouch is prepared in accordance with the method of Duling (Microvasc. Res., 5, 423–429, 1973) and Svensjö et al. (Uppsala. J. Med. Sci., 83, 71–79, 1978). The preparation is set up in an experimental bath and superfused at 6 ml/min with a physiological solution containing Hepes. The temperature of the physiological solution is maintained at 36.5° C. and a stream of gas (5% $CO_2$-95% $N_2$) is applied above the experimental bath in order to maintain the level of $pO_2$ of the solution between 12 and 15 mmHg and the pH at 7.4.

Thirty minutes after setting up the preparation, FITC-dextran (150,000 dalton, 50 mg/ml) is administered to the animal by the intravenous route at a dose of 250 mg/kg. The preparation is observed by the "intravital microscopy" method under UV light using a Leitz Ortholux II microscope.

After the injection of FITC-dextran, the preparation is subjected either to a local administration of an agent that induces permeability: histamine ($2\times10^{-6}M$) or leucotriene $B_4$ ($LTB_4$; $10^{-8}M$), or to a period of ischaemia (30 min) reperfusion.

The administration of those agents and the period of ischaemia cause "leaks" (visible as small fluorescent spots) throughout the preparation. The number of leaks is determined at several intervals after the administration of histamine or $LTB_4$ (from 2 to 30 min) and at 30 min of reperfusion after the ischaemia, and is expressed as the number of leaks per $cm^2$. The preparations are subjected several times (separated by at least 30 minutes) to a local administration of histamine or $LTB_4$.

Two types of study were carried out in order to determine the activity per os or the activity after i.v. administration of the compounds of the present invention.

1.1 Activity per os

The animals are treated by force-feeding, thirty minutes before anaesthesia, with different doses (from 1 to 100 mg/kg) of one of the compounds of the invention suspended in gum arabic. The dose of the compound is contained in 0.2 ml. The control animals receive a force-feed of 0.2 ml of gum arabic (placebo).

1.1.1 Activity per os at 100 mg/kg

The compounds of the invention administered at 100 mg/kg p.o. to the hamster, reduce significantly (t-test; *p<0,05) and in a lasting manner the extravasation of macromolecules caused by the histamine or $LTB_4$ in the microcirculation. The results obtained with histamine are summarised in Table 1. The results are superior to those obtained under the same operating conditions with the reference substance, proxerutine.

TABLE 1

Influence of the compounds of the invention on the extravasation of FITC-dextran in the hamster cheek pouch after treatment per os (100 mg/kg)

| at time t after administration | Number of leaks per $cm^2$ | | | |
|---|---|---|---|---|
| p.o. → | t = 3 h | t = 4 h | t = 5 h | t = 15 h |
| Placebo (n = 6) | 375 ± 6 | 373 ± 8 | 377 ± 4 | 354 ± 17 |
| Compound of Example 46 α form (n = 3) | 128 ± 13* | 157 ± 11* | 237 ± 10* | |
| Compound of Example 46 β form (n = 3) | 114 ± 11* | 99 ± 12* | 102 ± 14* | |
| Compound of Example 48 (n = 3) | 118 ± 3* | 154 ± 20* | 139 ± 20* | 142 ± 12* |
| Compound of Example 58 (n = 3) | 177 ± 24* | 258 ± 23* | 292 ± 23* | |
| Compound of Example 59 (n = 3) | 212 ± 29* | 256 ± 17* | 341 ± 11 | |
| Compound of Example 69 (n = 3) | 95 ± 20* | 84 ± 19* | 140 ± 4* | |
| Compound of Example 70 (n = 3) | 227 ± 17* | 156 ± 19* | 163 ± 27* | |
| Compound of Example 74 (n = 3) | 231 ± 13* | 305 ± 11* | | |
| proxerutine n = 3 | 374 ± 16 | 325 ± 11 | 309 ± 9 | |

*p < 0,05; Student t-test for non-paired values.

1.1.2 Activity per os: dose effect

The compounds of the invention, administered at doses of from 1 to 100 mg/kg p.o. to the hamster, reduce significantly and in a dose-dependent manner, starting from the lowest dose of 1 mg/kg, the extravasation of macromolecules, caused by histamine, in the micro-circulation. The results obtained 3 hours after administration p.o. are summarised in Table 2.

TABLE 2

Influence of the compounds of the invention on the extravasation of FITC-dextran in the hamster cheek pouch 3 hours after treatment per os: a dose-dependent effect is demonstrated (doses from 1 to 100 mg/kg)

| Dose (mg/kg) | Number of leaks per $cm^2$ | | |
|---|---|---|---|
| | Example 46 β form | Example 48 | Example 69 |
| 0 (placebo) | 373 ± 8 | 373 ± 8 | 373 ± 8 |
| 1 | 355 ± 8 | 310 ± 14 | 369 ± 22 |
| 3 | ND | 237 ± 3 | 294 ± 10 |
| 10 | 311 ± 21 | 227 ± 9 | 255 ± 9 |
| 30 | 204 ± 16 | 179 ± 20 | 181 ± 12 |
| 100 | 114 ± 11 | 118 ± 13 | 95 ± 20 |

ND: not-determined 1.1.3 Activity per os: leaks caused by ischaemia/reperfusion

The compounds of the invention, administered at doses of from 1 to 30 mg/kg p.o. to the hamster, reduce significantly and in a dose-dependent manner, from the lowest dose of 1 mg/kg, the extravasation of macromolecules caused by a period of ischaemia of 30 min. The results obtained 3 hours after the administration p.o. of the compounds are assembled in Table 3.

TABLE 3

Influence of the compounds of the invention on the extravasation of FITC-dextran in the hamster cheek pouch, caused by ischaemia, 3 hours after treatment per os.

| Dose (mg/kg) | Number of leaks/cm$^2$ | |
| --- | --- | --- |
| | Example 48 | Example 69 |
| 0 (placebo) | 123 ± 22 | 123 ± 22 |
| 1 | 78 ± 6 | 66 ± 8 |
| 3 | 48 ± 2 | 48 ± 6 |
| 10 | 42 ± 1 | 33 ± 12 |
| 30 | 19 ± 3 | ND |

1.2 I.v. activity

The compounds of the invention, dissolved in gum arabic, are administered at 10 mg/kg i.v. (0.2 ml of the solution+0,2 ml of a 0.9% NaCl solution). They reduce significantly and in a lasting manner the extravasation of macromolecules, caused by histamine, in the microcirculation. The results are shown in Table 4.

TABLE 4

Effect of the compounds of the invention on the extravasation of FITC-dextran in the hamster cheek pouch after administration at 10 mg/kg i.v.

| At time t after administration i.v. → | Number of leaks per cm$^2$** | | | | |
| --- | --- | --- | --- | --- | --- |
| | t = 0 min | t = 5 min | t = 40 min | t = 120 min | t = 180 min |
| Compound of Example 46 α form | 310 ± 36 | 69 ± 9* | 86 ± 34 | 226 ± 36* | 207 ± 41* |
| Compound of Example 46 β form | 397 ± 20 | 145 ± 32* | 40 ± 6* | 247 ± 21* | 234 ± 29* |
| Compound of Example 58 | 309 ± 19 | 161 ± 27* | 113 ± 21* | 174 ± 27* | 168 ± 10* |
| Compound of Example 69 | 380 ± 11 | 174 ± 23* | 174 ± 29* | 309 ± 26* | 345 ± 29 |

*p < 0.05, Student t-test for paired values
**n = 4 in each group.

2/Anti-inflammatory activity
2.1 Anti-inflammatory activity on a model of tracheo-bronchial inflammation induced by the inhalation of LPS.

The test consisted in studying the increase in the cell content of the alveolar washings of the guinea-pig (Hartley guinea-pigs, n=8 per group, one control group and one treated group) after exposure for twenty minutes to a solution of LPS (E. coli) at a concentration of 1.25 µg/ml. The animals are treated 24 hours before exposure to the aerosol and on the day of exposure itself. The animals are sacrificed 24 hours after the exposure and broncho-alveolar washing is carried out. The assessment criterion is the quantification of the total number of cells and of the number of polymorphonucleocytes in the washings.

Thus, the product forming the subject of Example 16, at a dose of 100 mg/kg per day p.o., brought about a significant decrease in the cell content of 25% and in the number of polymorphonucleocytes of 37%.

2.2 Anti-inflammatory activity on the model of mouse ear oedema induced by the topical administration of arachidonic acid.

The test consists in studying in the mouse (male CD1 mice (n=6/group) the increase in weight of the ear induced by the topical administration of arachidonic acid (1 mg, period 30 minutes) compared with the weight of the controlateral control ear. The assessment criterion is the difference in weight between the inflamed ear and the control ear.

The results are expressed as a % inhibition compared with a control group that has not received any product.

Thus, the product forming the subject of Example 16, at a dose of 20 mg/kg (p.o. 1 hour before the administration of arachidonic acid), brought about a significant inhibition of mouse ear oedema of 25%.

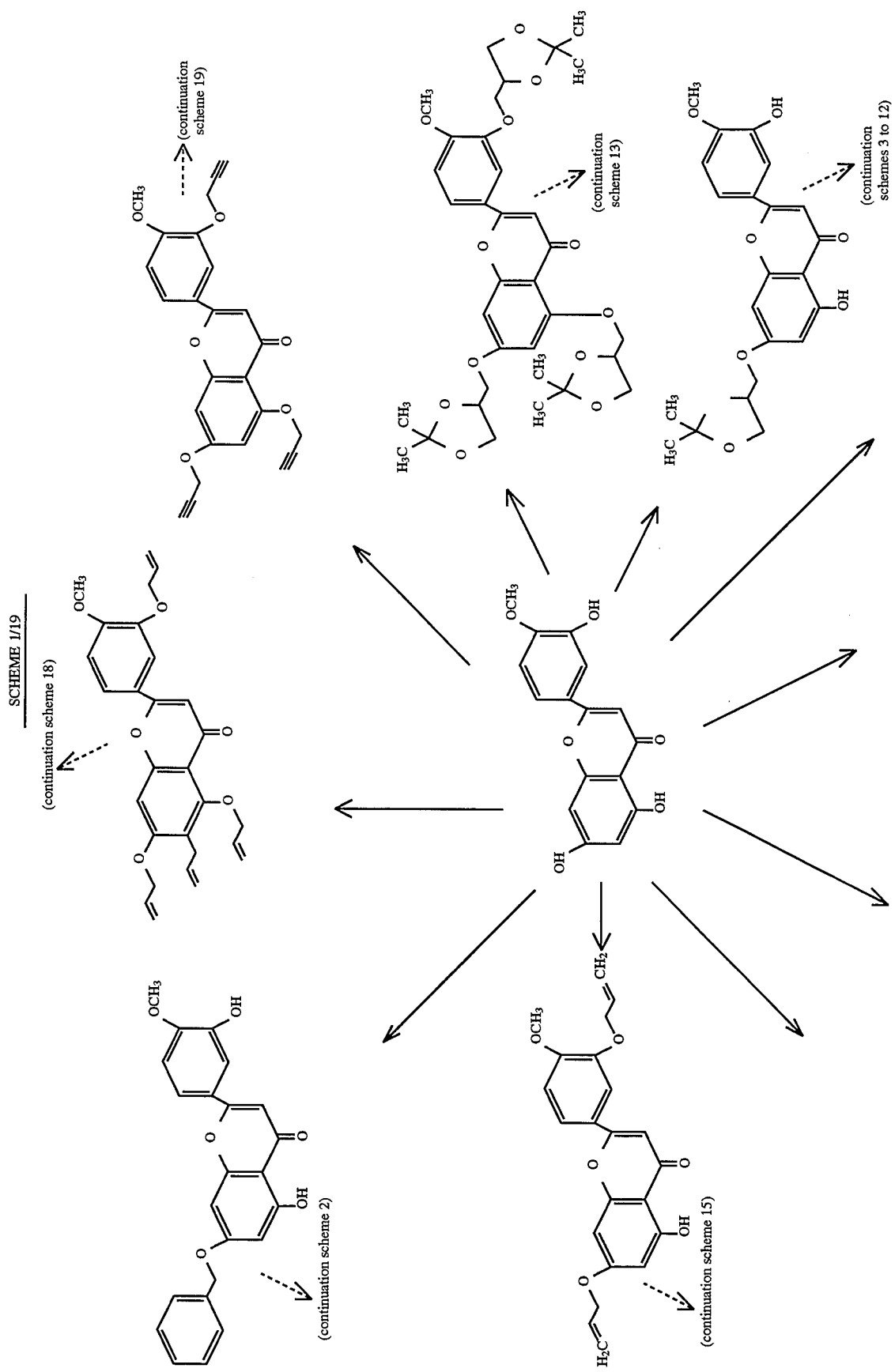

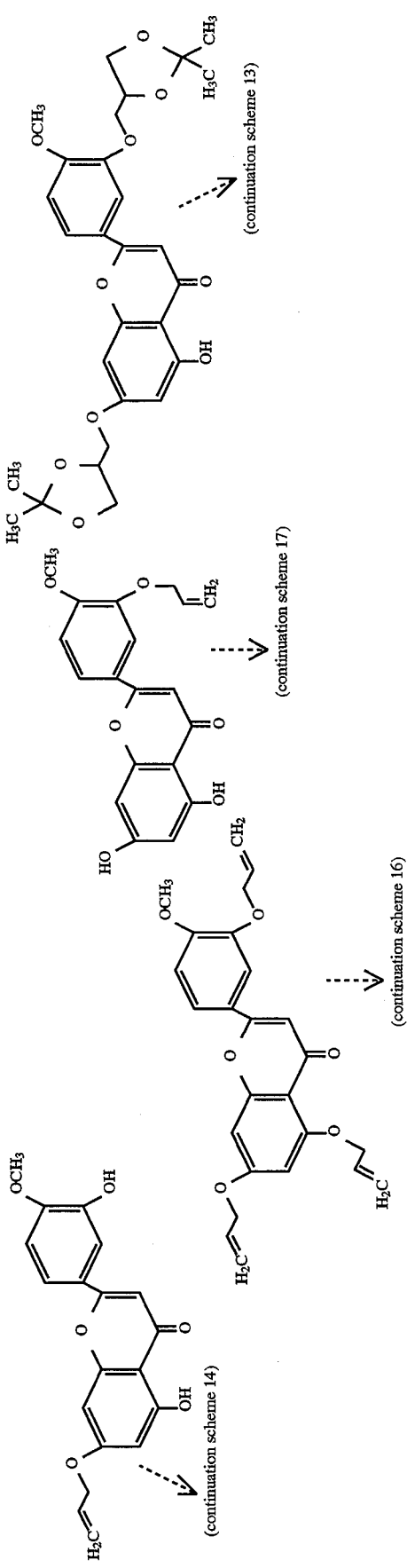
-continued
SCHEME 1/19

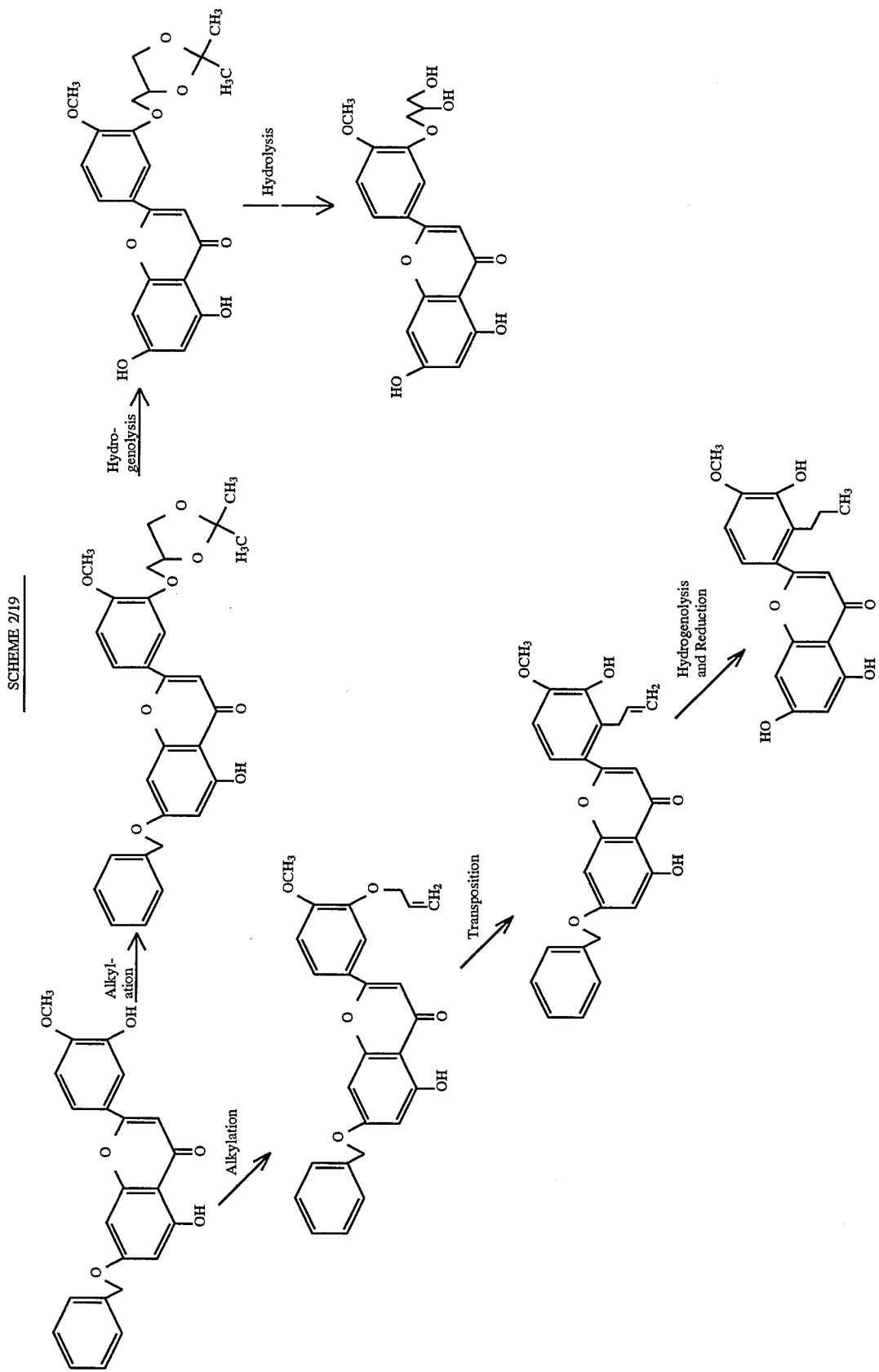

SCHEME 3/19
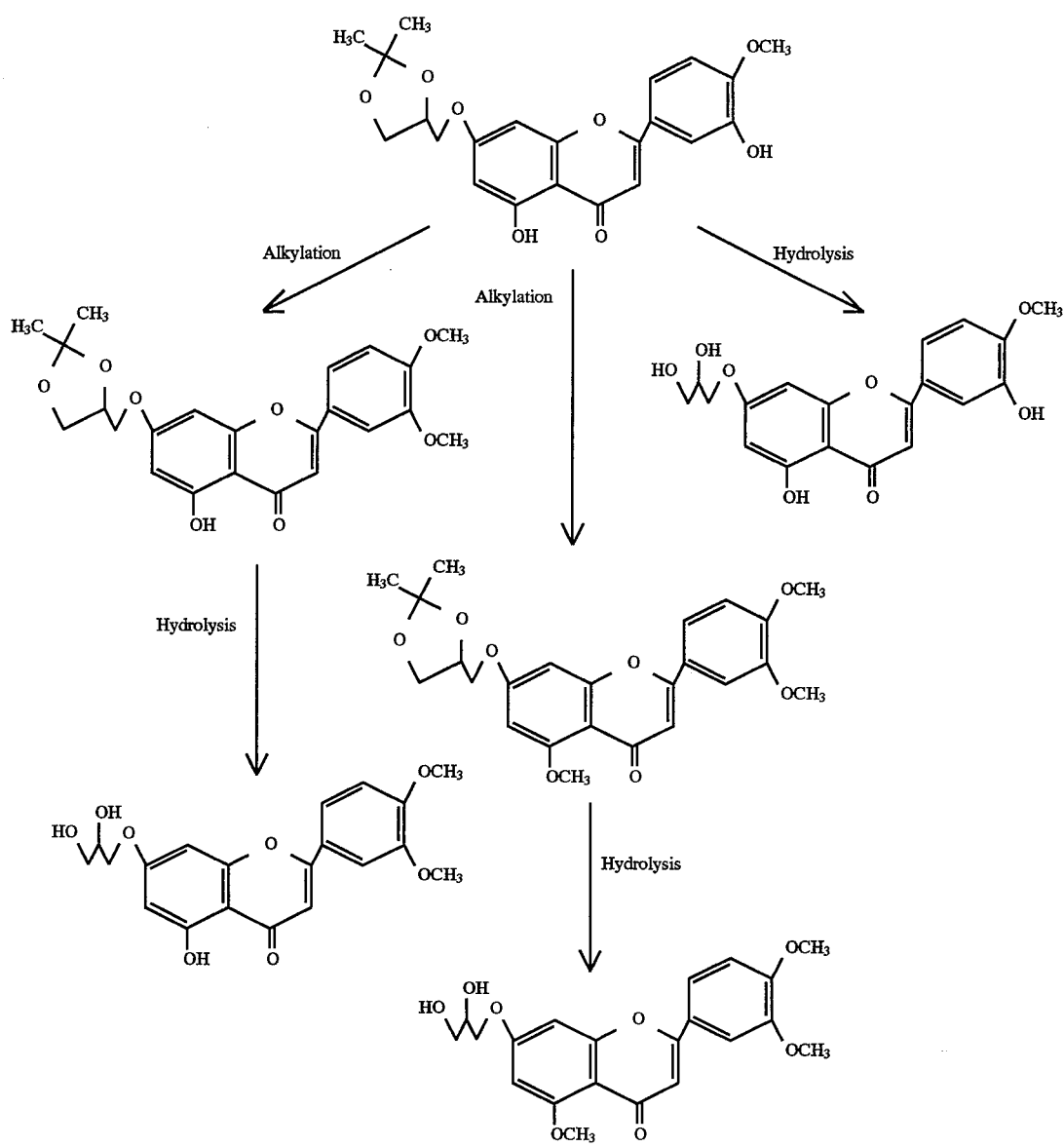
SCHEME 4/19
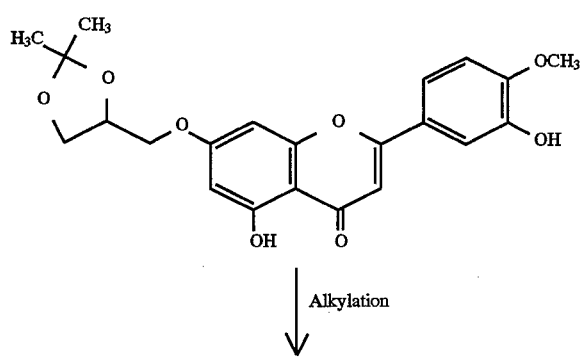

-continued
SCHEME 4/19
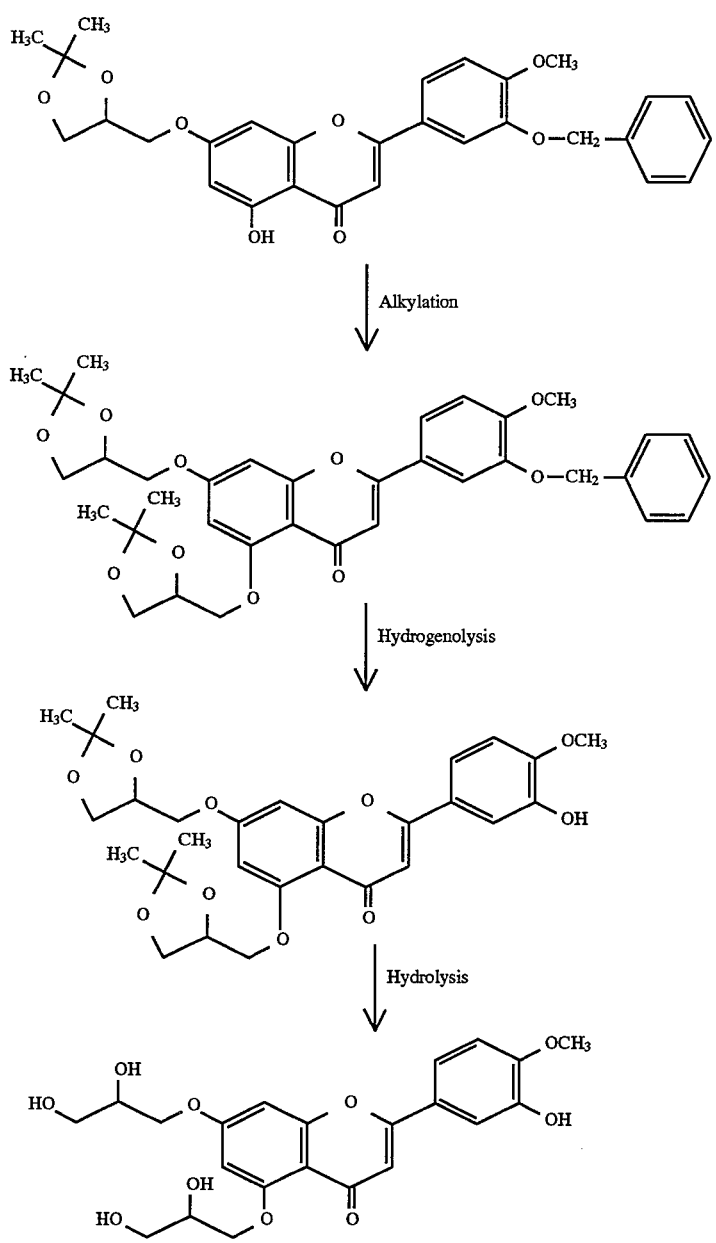
SCHEME 5/19
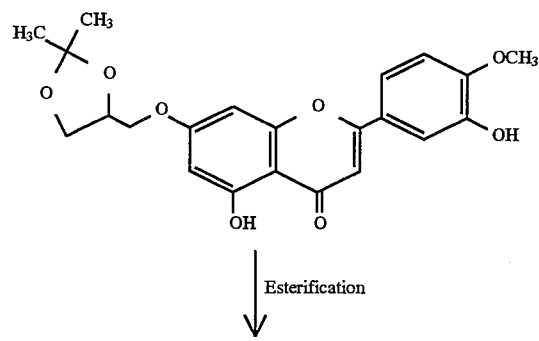
-continued
SCHEME 5/19
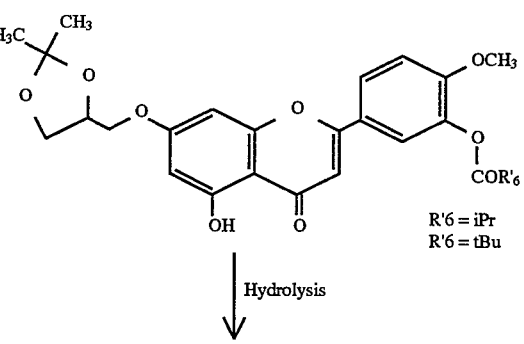

SCHEME 5/19
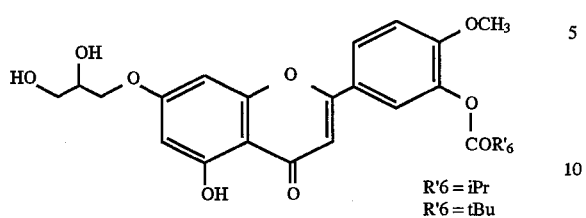
R'6 = iPr
R'6 = tBu
SCHEME 6/19
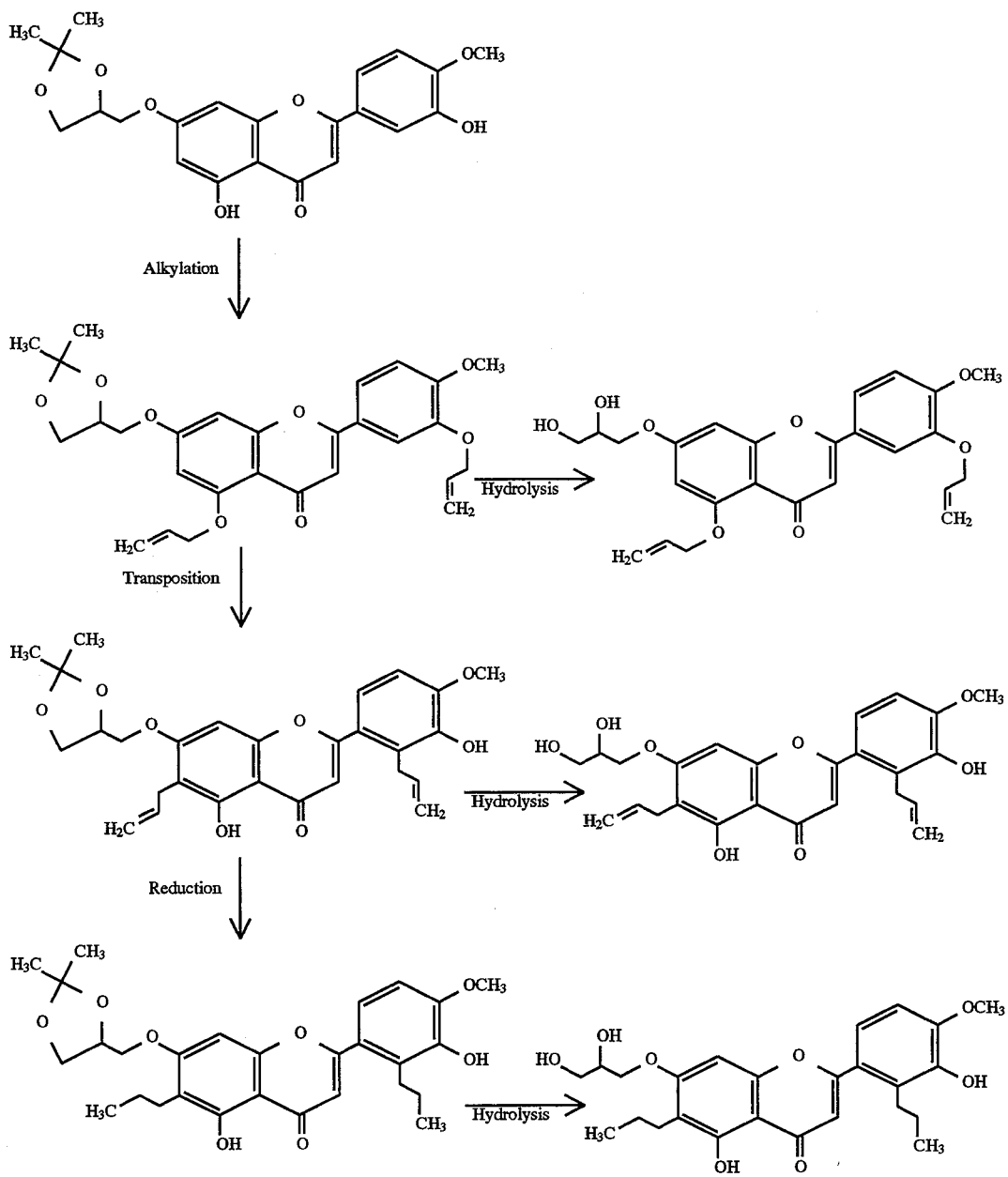

SCHEME 7/19
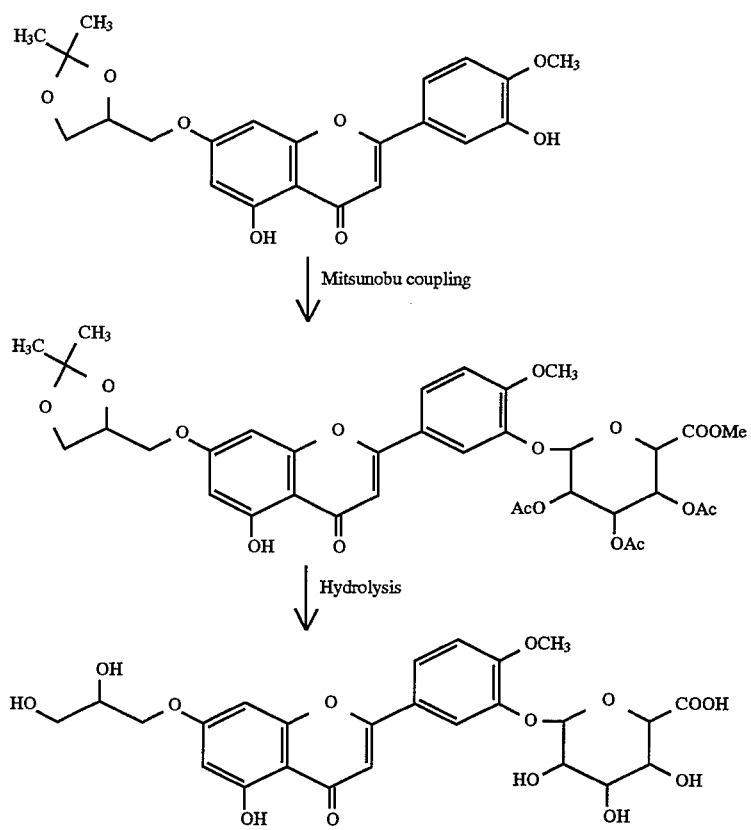

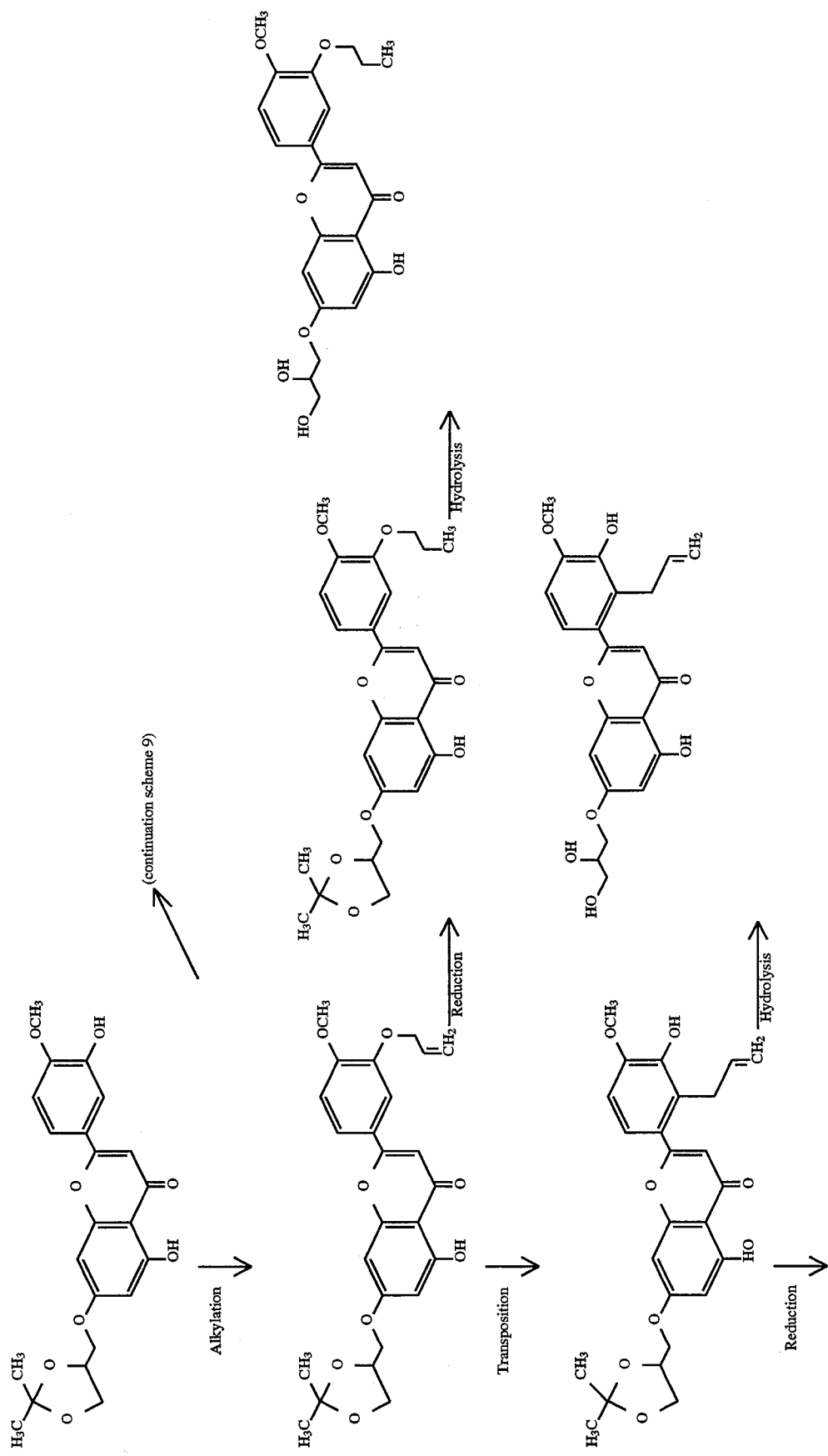

-continued
SCHEME 8/19
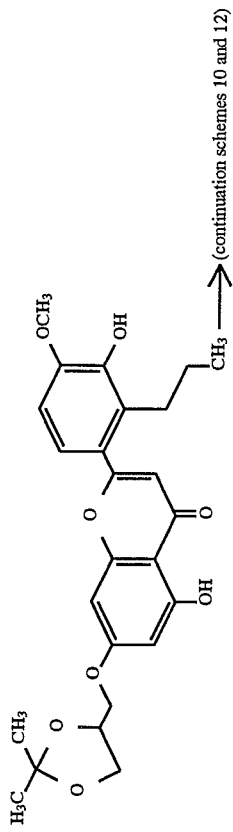
CH₃ ⟶ (continuation schemes 10 and 12)

SCHEME 9/19
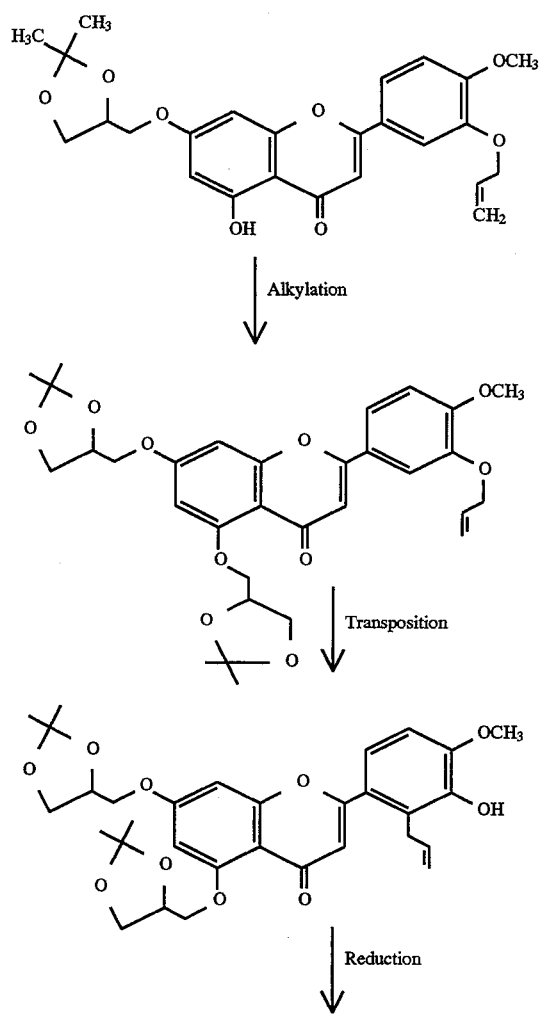
-continued
SCHEME 9/19
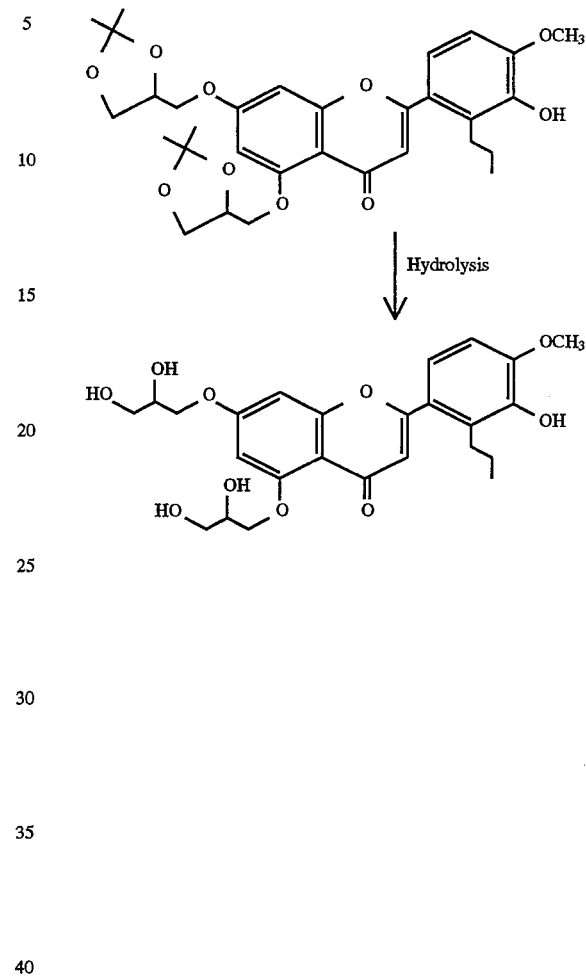
SCHEME 10/19
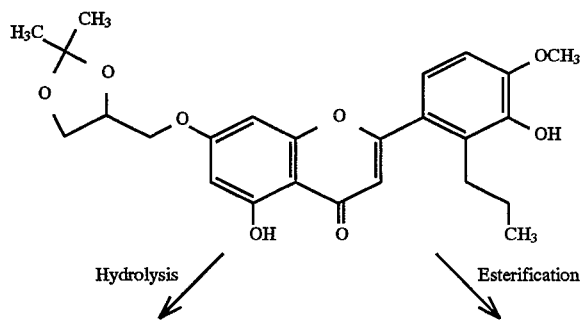

-continued
SCHEME 10/19
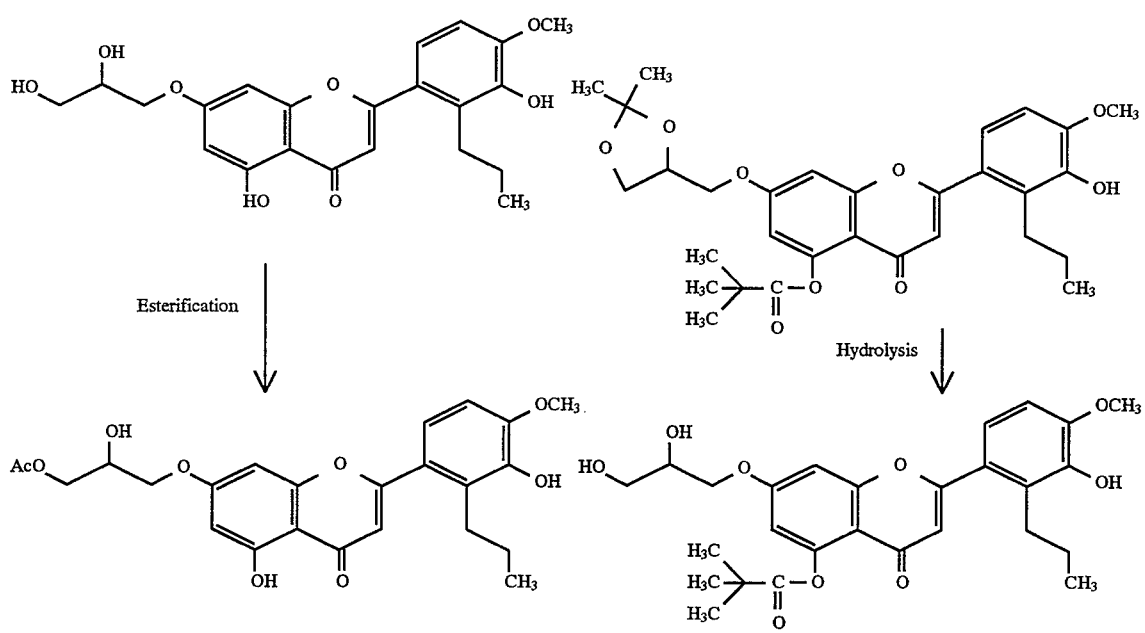
SCHEME 11/19
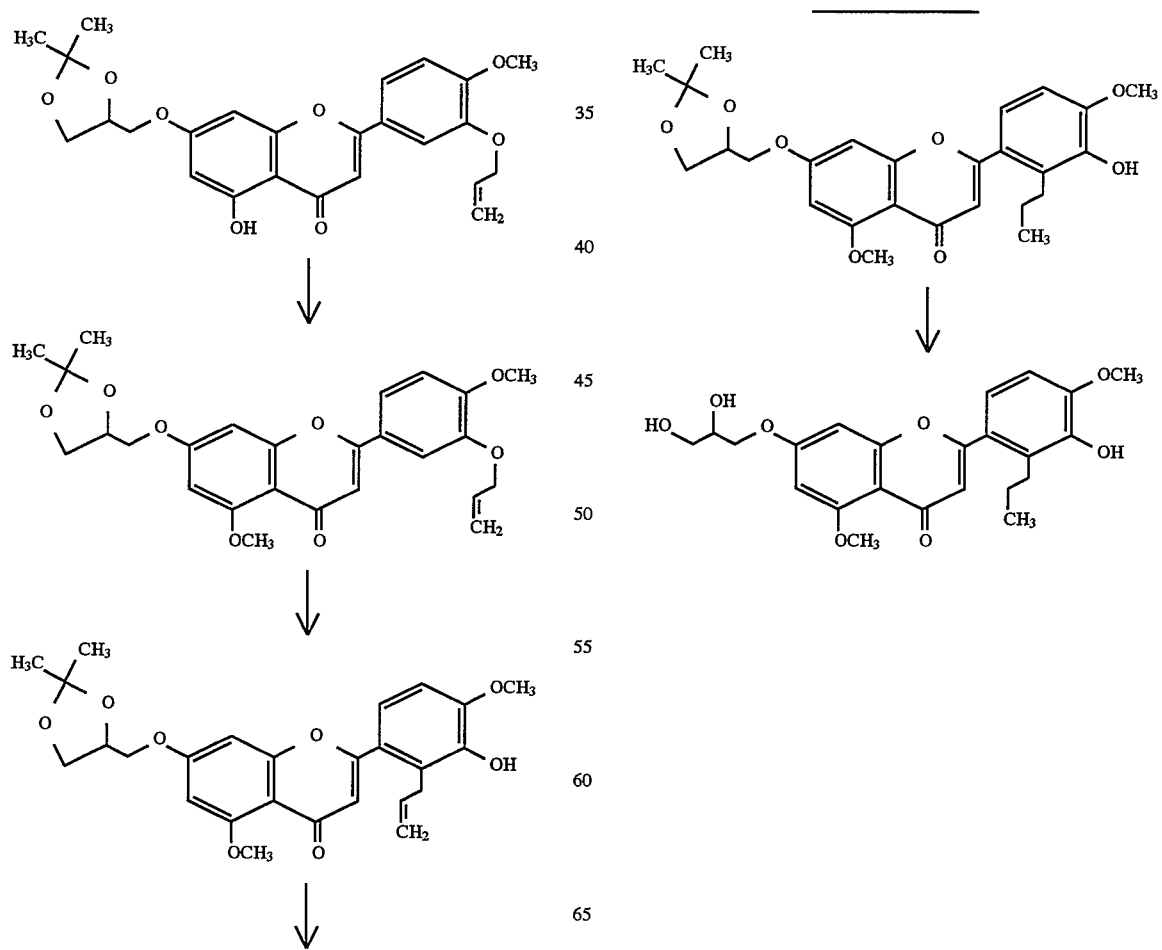
-continued
SCHEME 11/19

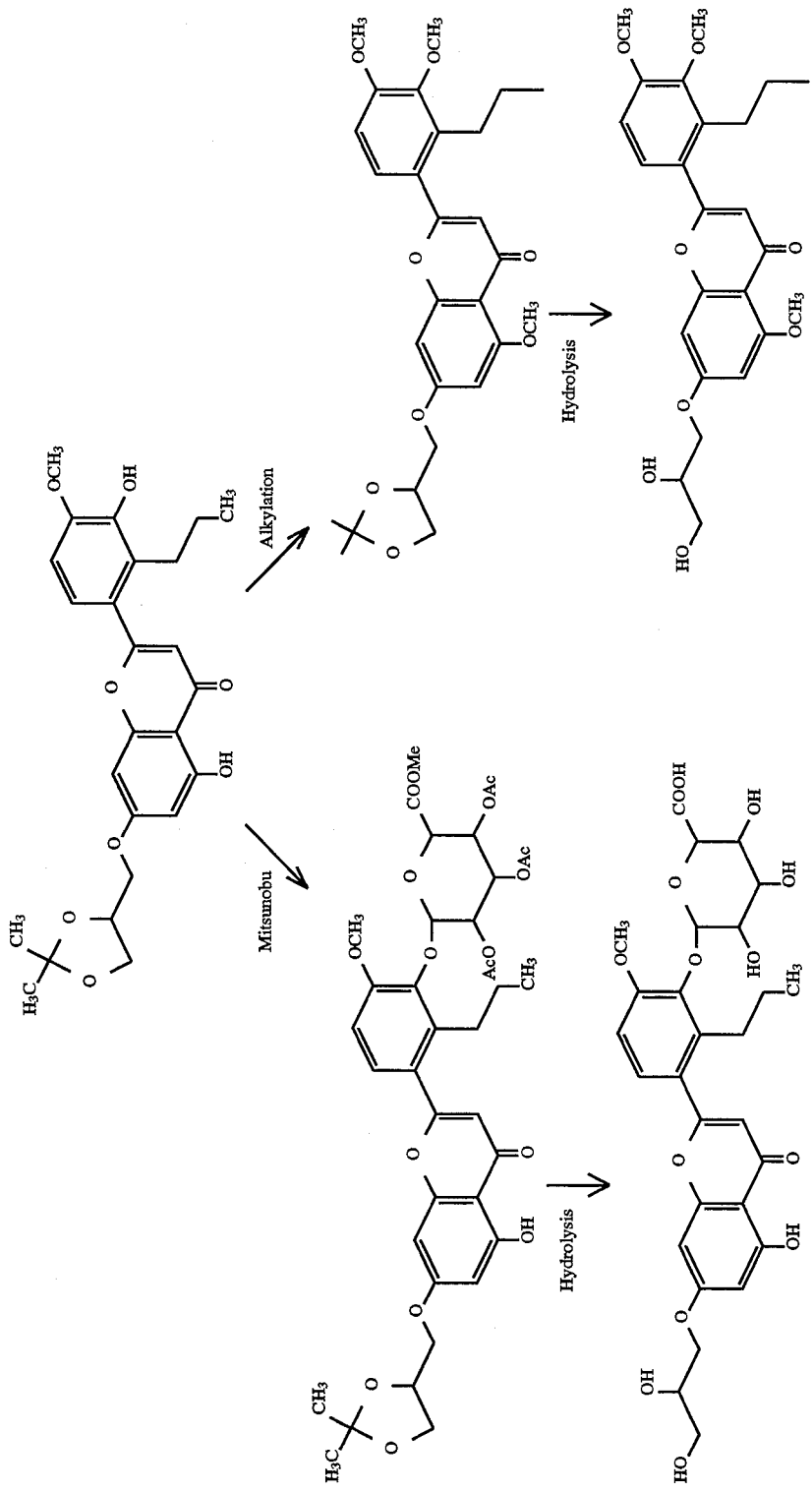

SCHEME 13/19
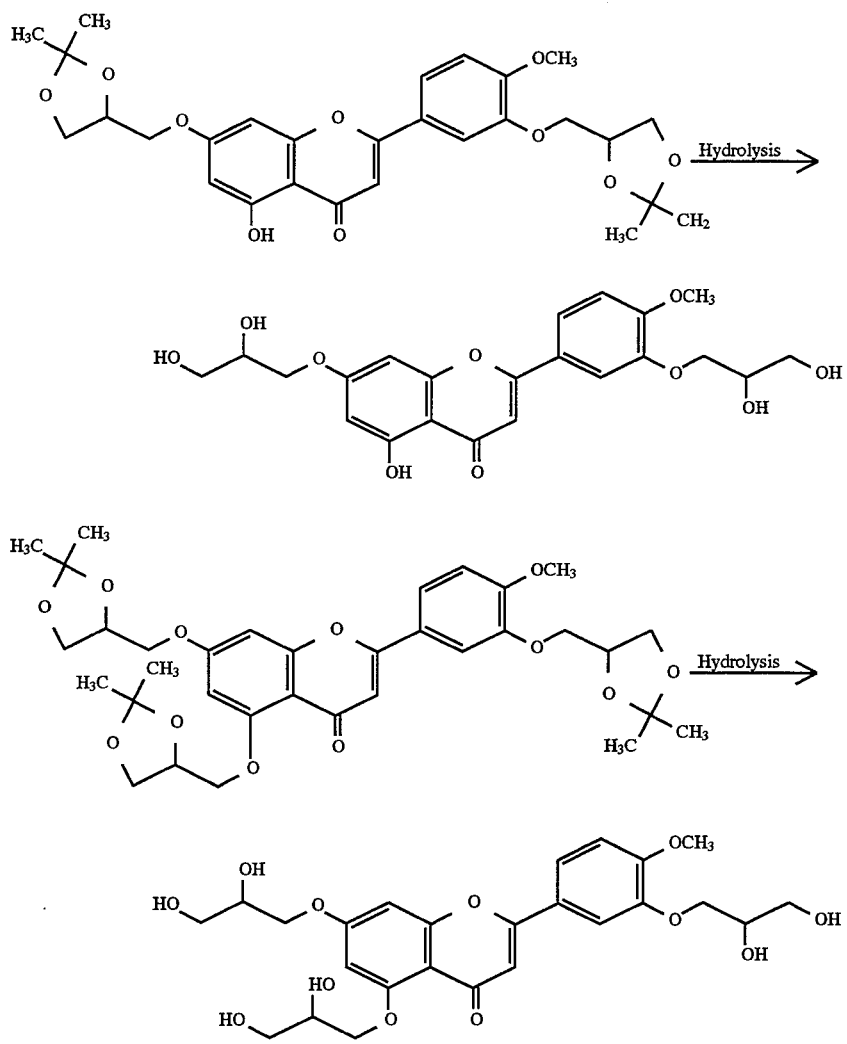
SCHEME 14/19
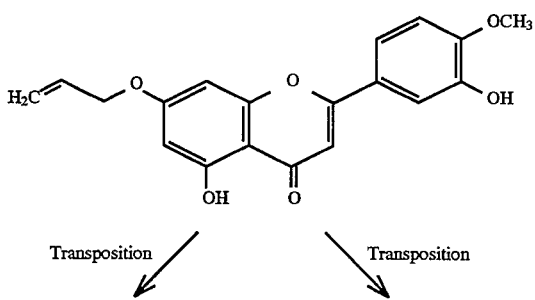

-continued
SCHEME 14/19
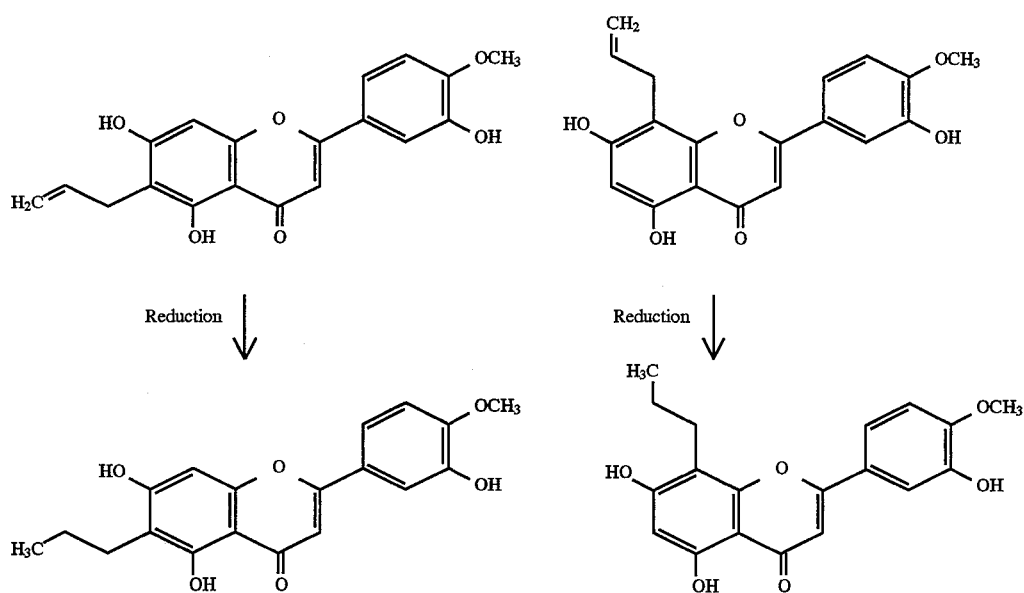
SCHEME 15/19
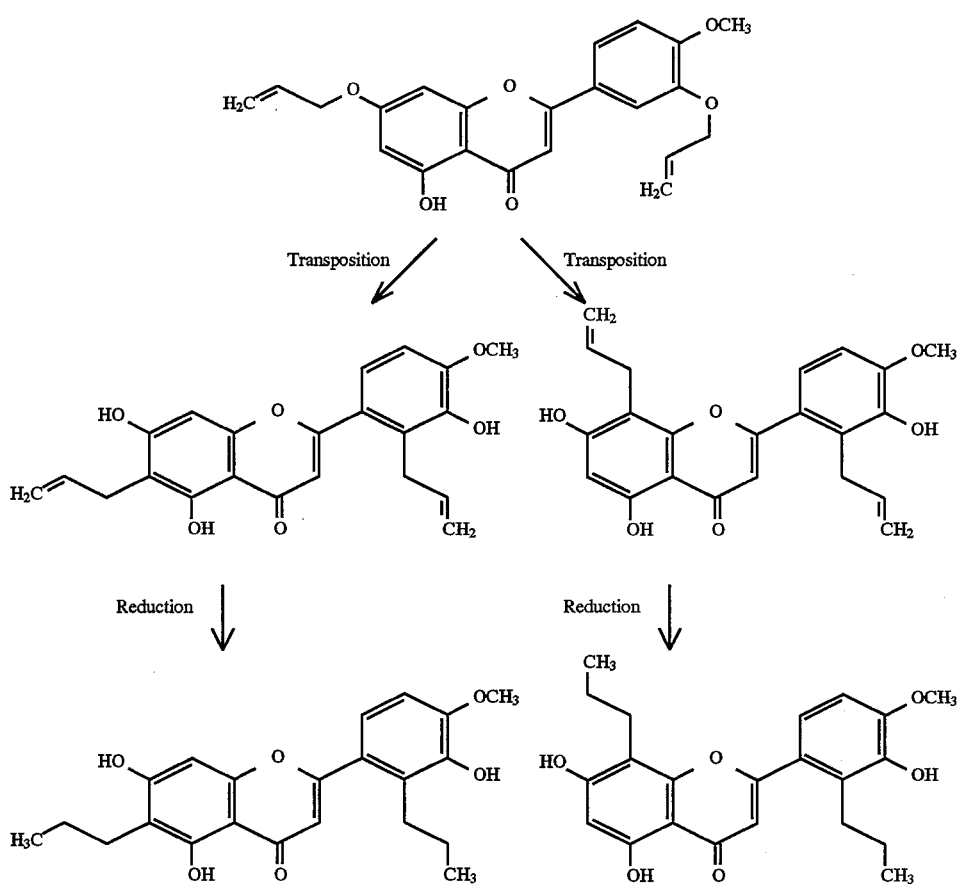

71
SCHEME 16/19
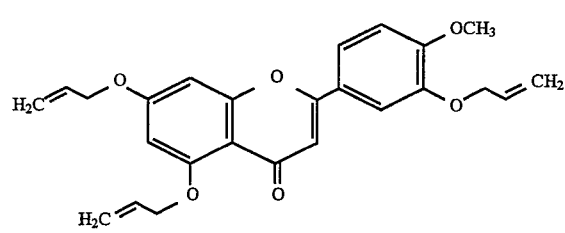
Transposition ↓
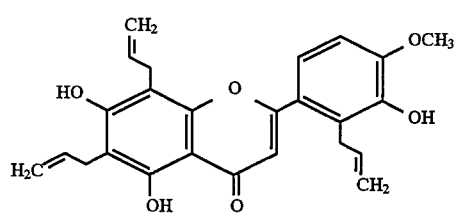
Reduction ↓
72
-continued
SCHEME 16/19
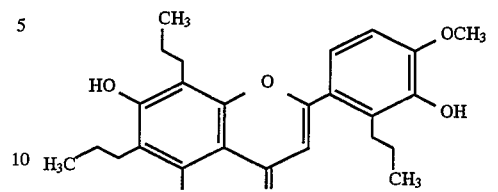
SCHEME 17/19
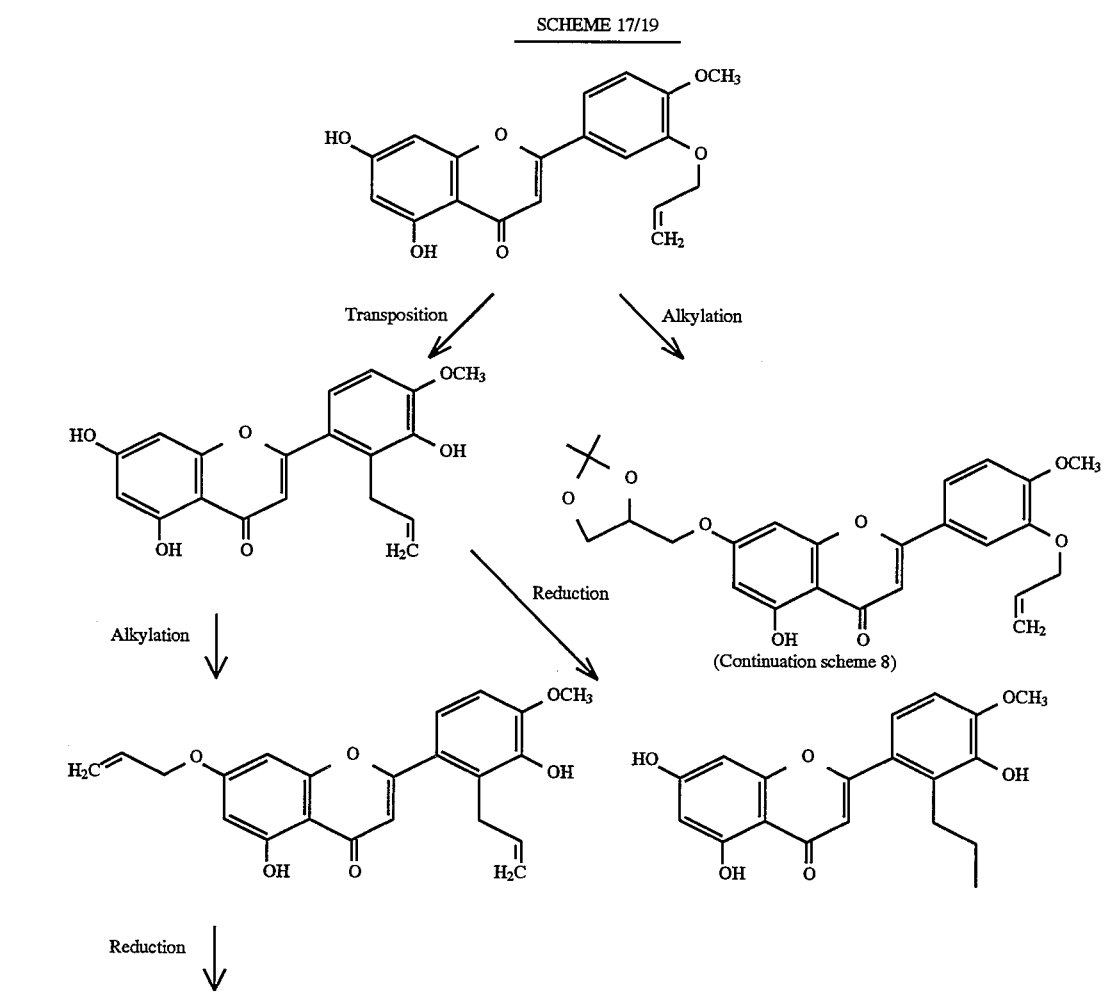

-continued
SCHEME 17/19
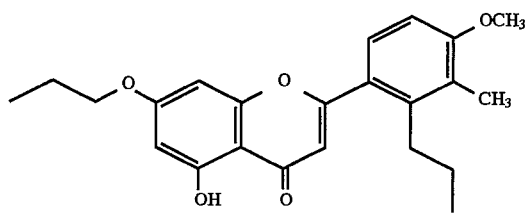
SCHEME 18/19
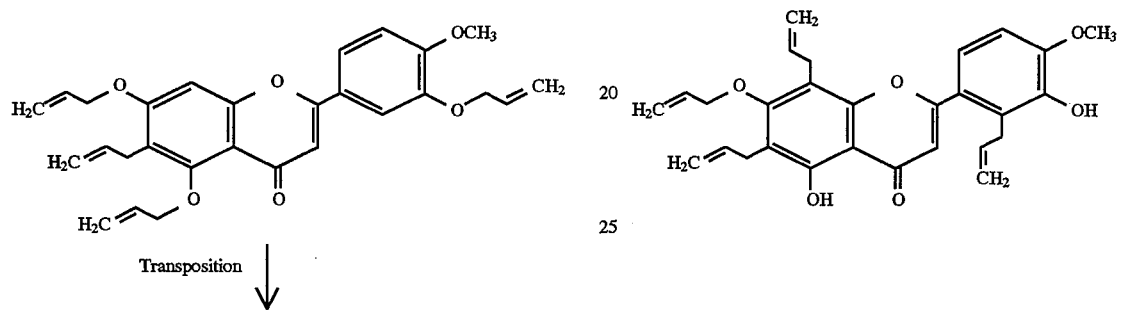
-continued
SCHEME 18/19
Transposition
SCHEME 19/19
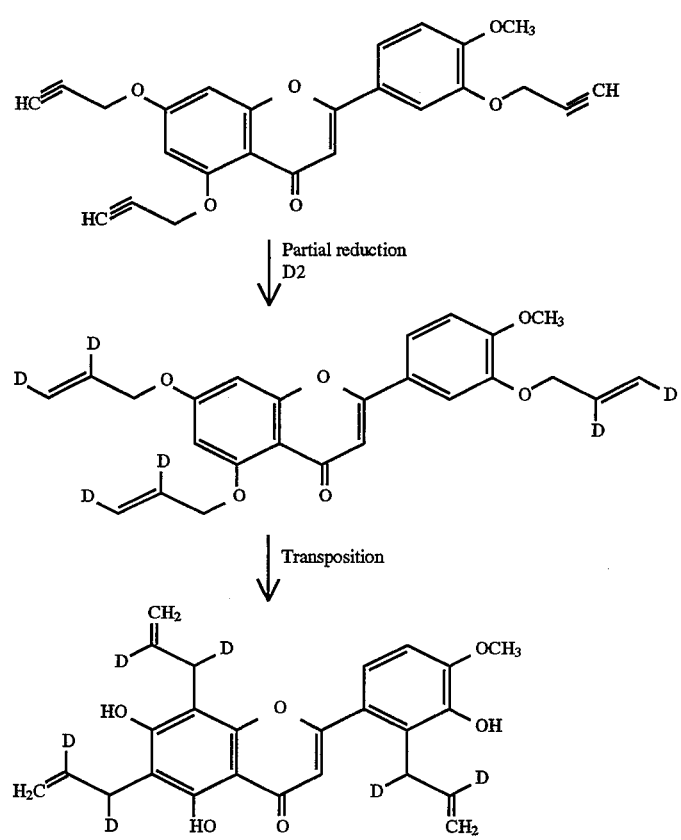
Partial reduction
D2
Transposition

We claim:
1. Diosmetin compounds selected from those of formula I:

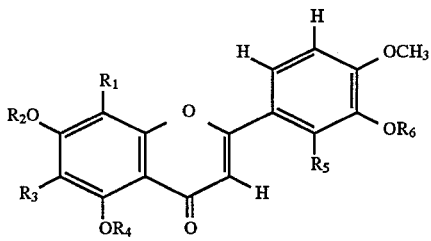

wherein:

R$_1$ represents hydrogen, allyl, or 1,2-dideuteroallyl;

R$_2$ represents hydrogen, allyl, propargyl, 2,3-dihydroxypropyl, (2,2-dimethyl-1,3-dioxol-4-yl)methyl, or 3-acetoxy-2-hydroxypropyl;

R$_3$ represents hydrogen, propyl, allyl or 1,2-dideuteroallyl;

R$_4$ represents hydrogen, allyl, propargyl, 2,3-dihydroxypropyl, (2,2-dimethyl-1,3-dioxol-4-yl)methyl, or —COR'$_4$, wherein R'$_4$ represents alkyl having 1 to 5 carbon atoms inclusive in straight or branched chain or phenyl;

R$_5$ represents hydrogen, propyl, allyl, 1,2-dideuteroallyl, and

R$_6$ represents hydrogen, allyl, or propargyl, 2,3-dihydroxypropyl, (2,2- dimethyl-1,3-dioxol-4-yl)methyl, or —COR'$_6$ wherein R'$_6$ represents alkyl having 1 to 5 carbon atoms inclusive in straight or branched chain, or phenyl, with the proviso that:
at least one of R$_1$, R$_2$, R$_3$, R$_4$, R$_5$ and R$_6$ has a meaning other than hydrogen,
if R$_1$, R$_2$ and R$_3$ each simultaneously represent hydrogen, then R$_4$ also represents hydrogen;
and, when R$_4$ is COR'$_4$ and/or R$_6$ is COR'$_6$ (R'$_4$ and R'$_6$ being as above-defined), then at least one of R$_1$, R$_2$, R$_3$, and R$_5$ is other than hydrogen or propyl;
and also their diastereoisomers and/or enantiomers.

2. A compound selected from the group consisting of 7-allyloxy-5-hydroxy-2-(3-allyloxy-4-methoxyphenyl)-4H-1-benzopyran-4-one, 5,7-dihydroxy-2-{3-[(2,3-dihydroxypropoxy)-4-methoxyphenyl}-4H-1-benzopyran-4-one, (R,S)-5-hydroxy-2-(3-hydroxy-4-methoxyphenyl)-7-(2,3-dihydroxypropoxy)-4H-1-benzopyran-4-one, 5,7-di-(2,3-dihydroxypropoxy)-2-(3-hydroxy-4-methoxyphenyl)-4H-1-benzopyran-4-one, 5-hydroxy-2-(4-methoxy-3-pivaloyloxyphenyl)-7-(2,3-dihydroxypropoxy)-4H-1-benzopyran-4-one, 5-allyloxy-2-(3-allyloxy-4-methoxyphenyl)-7-(2,3-dihydroxypropoxy)-4H-1-benzopyran-4-one, 6-allyl-5-hydroxy-2-(2-allyl-3-hydroxy-4-methoxyphenyl)-7-(2,3-dihydroxypropoxy)-4H-1-benzopyran-4-one, 5-hydroxy-2-(3-hydroxy-4-methoxy-2-propylphenyl)-6-propyl-7-(2,3-dihydroxypropoxy)-4H-1-benzopyran-4-one, (R,S)-5-hydroxy-2-(3-hydroxy-4-methoxy-2-propylphenyl)-7-(2,3-dihydroxypropoxy)-4H-1-benzopyran-4-one, in the two forms α and β, (R)-5-hydroxy-2-(3-hydroxy-4-methoxy-2-propylphenyl)-7-(2,3-dihydroxypropoxy)-4H-1-benzopyran-4-one, (S)-5-hydroxy-2-(3-hydroxy-4-methoxy-2-propylphenyl)-7-(2,3-dihydroxypropoxy)-4H-1-benzopyran-4-one, (R,S)-5-hydroxy-2-(3-hydroxy-4-methoxy-2-propylphenyl)-7-(3-acetoxy-2-hydroxypropoxy)-4H-1-benzopyran-4-one, 5-hydroxy-2-[4-methoxy-2-propyl-3-(6-carboxy-3,4,5-trihydroxytetrahydropyran-2-yloxy)phenyl]-7-(2,3-dihydroxypropoxy)-4H-1-benzopyran-4-one, 5-hydroxy-2-[4-methoxy-3-(2,3-dihydroxypropoxy)-phenyl]-7- (2,3-dihydroxypropoxy)-4H-1-benzopyran-4-one, 6,8-diallyl-5,7-dihydroxy-2-(2-allyl-3-hydroxy-4-methoxyphenyl)-4H-1-benzopyran-4-one, and 5,7-dihydroxy-2-(3-hydroxy-4-methoxy-2-propylphenyl)-6,8-dipropyl-4H-1-benzopyran-4-one.

3. A compound of claim 2, which is 7-allyloxy-5-hydroxy-2-(3-allyloxy-4-methoxyphenyl)4H-1-benzopyran-4-one.

4. A compound of claim 2, which is 5,7-dihydroxy-2-{3-[(2,3-dihydroxypropoxy)-4-methoxyphenyl}-4H-1-benzopyran-4-one.

5. A compound of claim 2, which is (R,S)-5-hydroxy-2-(3-hydroxy-4-methoxyphenyl)-7-(2,3-dihydroxypropoxy)-4H-1-benzopyran-4-one.

6. A compound of claim 2, which is 5,7-di-(2,3-dihydroxypropoxy)-2-(3-hydroxy-4-methoxyphenyl)-4H-1-benzopyran-4-one.

7. A compound of claim 2, which is 5-hydroxy-2-(4-methoxy-3-pivaloyloxyphenyl)-7-(2,3-dihydroxypropoxy)-4H-1-benzopyran-4-one.

8. A compound of claim 2, which is 5-allyloxy-2-(3-allyloxy-4-methoxyphenyl)-7-(2,3-dihydroxypropoxy)-4H-1-benzopyran-4-one.

9. A compound of claim 2, which is 6-allyl-5-hydroxy-2-(2-allyl-3-hydroxy-4-methoxyphenyl)-7-(2,3-dihydroxypropoxy)-4H-1-benzopyran-4-one.

10. A compound of claim 2, which is 5-hydroxy-2-(3-hydroxy-4-methoxy-2-propylphenyl)-6- propyl-7-(2,3-dihydroxypropoxy)-4H-1-benzopyran-4-one.

11. A compound of claim 2, which is (R,S)-5-hydroxy-2-(3-hydroxy-4-methoxy-2-propylphenyl)-7-(2,3-dihydroxypropoxy)-4H-1-benzopyran-4-one, in the two forms α and β.

12. A compound of claim 2, which is (R)-5-hydroxy-2-(3-hydroxy-4-methoxy-2-propylphenyl)-7-(2,3-dihydroxypropoxy)-4H-1-benzopyran-4-one.

13. A compound of claim 2, which is (S)-5-hydroxy-2-(3-hydroxy-4-methoxy-2-propylphenyl)-7-(2,3-dihydroxypropoxy)-4H-1-benzopyran-4-one.

14. A compound of claim 2, which is (R,S)-5-hydroxy-2-(3-hydroxy-4-methoxy-2-propylphenyl)-7-(3-acetoxy-2-hydroxypropoxy)-4H-1-benzopyran-4-one.

15. A compound of claim 2, which is 5-hydroxy-2-[4-methoxy-2-propyl-3-(6-carboxy-3,4,5-trihydroxytetrahydropyran-2-yloxy)phenyl]-7-(2,3-dihydroxypropoxy)-4H-1-benzopyran-4-one.

16. A compound of claim 2, which is 5-hydroxy-2-[4-methoxy-3-(2,3-dihydroxypropoxy)phenyl]-7-(2,3-dihydroxypropoxy)-4H-1-benzopyran-4-one.

17. A compound of claim 2, which is 6,8-diallyl-5,7-dihydroxy-2-(2-allyl-3-hydroxy-4-methoxyphenyl)-4H-1-benzopyran-4-one.

18. A compound of claim 2, which is 5,7-dihydroxy-2-(3-hydroxy-4-methoxy-2-propylphenyl)-6,8-dipropyl-4H-1-benzopyran-4-one.

19. A method, for treating an animal or human living animal body afflicted with chronic venous insufficiency, comprising the step of administering to the living animal body an amount of a compound of claim 1 which is effective for alleviation of said condition.

20. A pharmaceutical composition, useful in alleviation of chromic venous insufficiency comprising as active ingredient an effective amount of a compound of claim 1, together with one or more pharmaceutically acceptable excipients or vehicles.

21. A method, for treating an animal or human living animal body afflicted with chronic venous insufficiency, comprising the step of administering to the living animal body an amount of a compound of claim 2 which is effective for alleviation of said condition.

22. A pharmaceutical composition, useful in alleviation of chronic venous insufficiency, comprising as active ingredient an effective amount of a compound of claim 2, together with one or more pharmaceutically-acceptable excipients or vehicles.

* * * * *

UNITED STATES PATENT AND TRADEMARK OFFICE
CERTIFICATE OF CORRECTION

PATENT NO. : 5,629,339
DATED : Mat 13, 1997
INVENTOR(S) : M. Wierzbicki, M.F. Boussard, T. Verbeuren, M.O. Vallez, E. Canet, Y. Rolland It is certified that error appears in the above-identified patent and that said Letters Patent is hereby corrected as shown below:

Column 30, line 31:   "13" should read -- ß --.

Column 33, line 56:   "(2,2-dimethylol-" should read
    -- (2,2-dimethyl- --.

Column 44, top of page, far right: "(continuation schemes
    3 to 12)":   Scheme should read as follows:

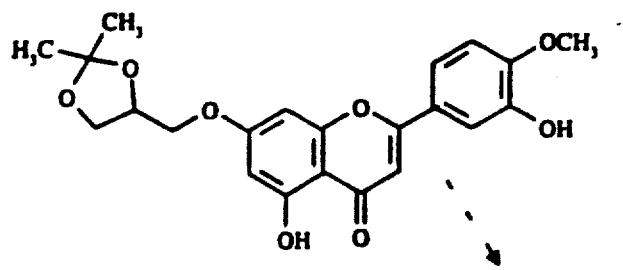

(continuation schemes 3 to 12)

Column 75, line 15:   Insert -- propyl, -- between
    "hydrogen," and "allyl,".

UNITED STATES PATENT AND TRADEMARK OFFICE
CERTIFICATE OF CORRECTION

PATENT NO. : 5,629,339
DATED : Mat 13, 1997
INVENTOR(S) : M. Wierzbicki, M.F. Boussard, T. Verbeuren, M.O. Vallez, E. Canet, Y. Rolland It is certified that error appears in the above-identified patent and that said Letters Patent is hereby corrected as shown below:

Column 75, line 26: Insert the word "or" after "allyl,".

Column 75, line 28: Delete the word "or" after "allyl,".

Signed and Sealed this

Twenty-third Day of December, 1997

*Attest:*

BRUCE LEHMAN

*Attesting Officer*    *Commissioner of Patents and Trademarks*